US010188035B2

(12) United States Patent
Reich et al.

(10) Patent No.: US 10,188,035 B2
(45) Date of Patent: Jan. 29, 2019

(54) LOAD-BASED YIELD SENSOR

(71) Applicant: Intelligent Agricultural Solutions, LLC, Fargo, ND (US)

(72) Inventors: Adam A. Reich, Fargo, ND (US); Paul A. Nystuen, West Fargo, ND (US)

(73) Assignee: Intelligent Agricultural Solutions LLC, Fargo, ND (US)

( * ) Notice: Subject to any disclaimer, the term of this patent is extended or adjusted under 35 U.S.C. 154(b) by 311 days.

(21) Appl. No.: 14/853,982

(22) Filed: Sep. 14, 2015

(65) Prior Publication Data

US 2016/0073583 A1    Mar. 17, 2016

Related U.S. Application Data

(60) Provisional application No. 62/049,616, filed on Sep. 12, 2014.

(51) Int. Cl.
*A01D 41/127* (2006.01)
*G01G 19/08* (2006.01)
(Continued)

(52) U.S. Cl.
CPC ....... *A01D 41/127* (2013.01); *A01D 41/1271* (2013.01); *A01D 41/1272* (2013.01); *A01D 41/1277* (2013.01); *A01D 57/12* (2013.01); *B65G 43/08* (2013.01); *G01B 7/14* (2013.01); *G01G 19/08* (2013.01); *G01L 1/00* (2013.01); *G01N 33/0098* (2013.01); *G01S 13/865* (2013.01); *G01S 13/867* (2013.01); *G01S 13/87* (2013.01); *G01S 13/88* (2013.01); *G01S 17/026* (2013.01); *G01S 17/88* (2013.01);
(Continued)

(58) Field of Classification Search
CPC ...... A01D 41/127; A01D 61/02; B65G 43/08; G01G 19/20; G01G 19/12
See application file for complete search history.

(56) References Cited

U.S. PATENT DOCUMENTS

| 4,004,289 | A | 1/1977 | Kirk |
| 4,057,709 | A | 11/1977 | Lyngsgaard et al. |
| | | (Continued) | |

FOREIGN PATENT DOCUMENTS

| AU | 2002214504 | 10/2004 |
| CA | 1184647 | 3/1985 |
| | (Continued) | |

OTHER PUBLICATIONS

"International Search Report and Written Opinion", PCT/US2015/050060, dated Dec. 15, 2015, pp. 1-6.
(Continued)

*Primary Examiner* — Matthew G Marini

(57) ABSTRACT

A method of estimating the mass of crop entering into a grain tank on a harvesting machine, comprising the steps of mounting a load sensor on the upper bearing of a conveyor belt moving crop through the clean grain elevator into the grain tank, connecting the load sensor to a processor, using the load sensor to measure a load on the conveyor belt when no crop is present in the clean grain elevator, and also when crop is moving through the clean grain elevator, and comparing the load with no crop present to the load when crop is present to estimate the mass of crop moving through the clean grain elevator.

7 Claims, 32 Drawing Sheets

(51) Int. Cl.

| | |
|---|---|
| *A01D 57/12* | (2006.01) |
| *G01B 7/14* | (2006.01) |
| *G01N 33/00* | (2006.01) |
| *G01S 13/86* | (2006.01) |
| *G01S 13/87* | (2006.01) |
| *G01S 17/02* | (2006.01) |
| *G01S 17/88* | (2006.01) |
| *G06K 9/00* | (2006.01) |
| *H04N 5/225* | (2006.01) |
| *G06T 7/00* | (2017.01) |
| *B65G 43/08* | (2006.01) |
| *G01L 1/00* | (2006.01) |
| *G01S 17/89* | (2006.01) |
| *G01S 13/88* | (2006.01) |
| *G06T 7/11* | (2017.01) |
| *G06T 7/136* | (2017.01) |
| *H04N 5/232* | (2006.01) |

(52) U.S. Cl.
CPC .......... *G01S 17/89* (2013.01); *G06K 9/00791* (2013.01); *G06T 7/0004* (2013.01); *G06T 7/11* (2017.01); *G06T 7/136* (2017.01); *H04N 5/2256* (2013.01); *A01D 41/1273* (2013.01); *A01D 41/1274* (2013.01); *A01D 41/1276* (2013.01); *G06K 2209/17* (2013.01); *G06T 2207/10004* (2013.01); *G06T 2207/10024* (2013.01); *G06T 2207/30128* (2013.01); *H04N 5/23229* (2013.01)

(56) References Cited

U.S. PATENT DOCUMENTS

| | | | |
|---|---|---|---|
| 4,243,054 A * | 1/1981 | Graalmann | A24C 5/397 131/108 |
| 4,259,020 A | 3/1981 | Babb | |
| 4,275,546 A * | 6/1981 | Bohman | A01D 75/187 460/2 |
| 4,348,855 A | 9/1982 | Depauw et al. | |
| 4,360,998 A | 11/1982 | Somes | |
| 4,421,772 A | 12/1983 | Munck et al. | |
| 4,441,513 A | 4/1984 | Herwig | |
| 4,527,241 A | 7/1985 | Sheehan et al. | |
| 4,713,781 A | 12/1987 | Brizgis et al. | |
| 4,765,190 A | 8/1988 | Strubbe | |
| 4,806,764 A | 2/1989 | Satake | |
| 4,951,031 A | 8/1990 | Strubbe | |
| 5,132,538 A | 7/1992 | Norris | |
| 5,561,250 A | 10/1996 | Myers | |
| 5,586,033 A | 12/1996 | Hall | |
| 5,751,421 A | 5/1998 | Wright et al. | |
| 5,835,206 A | 11/1998 | Tragesser | |
| 5,917,927 A | 6/1999 | Satake et al. | |
| 5,978,720 A | 11/1999 | Hieronymus et al. | |
| 5,995,894 A | 11/1999 | Wendte | |
| 6,009,186 A | 12/1999 | Gorretta et al. | |
| 6,100,526 A | 8/2000 | Mayes | |
| 6,119,442 A | 9/2000 | Hale | |
| 6,205,384 B1 | 3/2001 | Diekhans | |
| 6,269,618 B1 | 8/2001 | Digman et al. | |
| 6,282,476 B1 | 8/2001 | Hieronymus et al. | |
| 6,313,414 B1 * | 11/2001 | Campbell | G01G 19/08 177/136 |
| 6,421,990 B1 | 7/2002 | Ohlemeyer et al. | |
| 6,427,128 B1 | 7/2002 | Satake et al. | |
| 6,442,916 B1 | 9/2002 | Pope | |
| 6,449,932 B1 | 9/2002 | Cooper et al. | |
| 6,452,157 B1 | 9/2002 | Hosel | |
| 6,524,183 B1 | 2/2003 | Van Quekelberghe | |
| 6,591,145 B1 | 7/2003 | Hoskinson et al. | |
| 6,683,970 B1 | 1/2004 | Satake et al. | |
| 6,726,559 B2 | 4/2004 | Bischoff | |
| 6,931,828 B2 | 8/2005 | Kormann | |
| 7,169,040 B2 | 1/2007 | Kormann et al. | |
| 7,367,880 B2 | 5/2008 | Hoskinson et al. | |
| 7,372,034 B2 | 5/2008 | Kormann et al. | |
| 7,496,228 B2 | 2/2009 | Landwehr et al. | |
| 7,654,141 B2 | 2/2010 | Behnke et al. | |
| 7,804,588 B2 | 9/2010 | Kormann et al. | |
| 7,830,530 B2 | 11/2010 | Jonasson Bjarang | |
| 7,877,969 B2 | 2/2011 | Behnke | |
| 7,993,187 B2 | 8/2011 | Ricketts et al. | |
| 8,045,168 B2 | 10/2011 | Missotten et al. | |
| 8,086,378 B2 | 12/2011 | Behnke | |
| 8,115,923 B2 | 2/2012 | Priesnitz et al. | |
| 8,118,649 B1 | 2/2012 | Murray | |
| 8,139,824 B2 | 3/2012 | Missotten et al. | |
| 8,282,453 B1 | 10/2012 | Hillen et al. | |
| 8,337,283 B2 | 12/2012 | Kormann et al. | |
| 8,469,784 B1 | 6/2013 | Hoskinson et al. | |
| 9,125,344 B2 | 9/2015 | Baumgarten | |
| 9,253,941 B2 | 2/2016 | Clark | |
| 9,301,446 B2 | 4/2016 | Peters et al. | |
| 9,485,905 B2 | 11/2016 | Jung et al. | |
| 2002/0091476 A1 | 7/2002 | Beck | |
| 2002/0147534 A1 * | 10/2002 | Delcheccolo | B60K 31/0008 701/45 |
| 2003/0004630 A1 | 1/2003 | Beck | |
| 2005/0026662 A1 | 2/2005 | Fechner | |
| 2005/0033454 A1 | 2/2005 | Fitzner | |
| 2005/0137003 A1 | 6/2005 | Behnke | |
| 2005/0150202 A1 | 7/2005 | Quick | |
| 2005/0251347 A1 | 11/2005 | Perona et al. | |
| 2006/0009269 A1 | 1/2006 | Hoskinson | |
| 2006/0271243 A1 | 11/2006 | Behnke | |
| 2006/0272307 A1 | 12/2006 | Behnke | |
| 2006/0277882 A1 | 12/2006 | Berger et al. | |
| 2006/0277883 A1 | 12/2006 | Berger et al. | |
| 2008/0295471 A1 | 12/2008 | Polklas et al. | |
| 2009/0088932 A1 | 4/2009 | Diekhans | |
| 2009/0125197 A1 | 5/2009 | Behnke | |
| 2009/0258684 A1 | 10/2009 | Missotten et al. | |
| 2009/0325658 A1 | 12/2009 | Phelan | |
| 2010/0071329 A1 | 3/2010 | Hindryckz | |
| 2010/0125788 A1 | 5/2010 | Hieronymus | |
| 2010/0217474 A1 | 8/2010 | Baumgarten et al. | |
| 2010/0217481 A1 | 8/2010 | Baumgarten | |
| 2012/0004815 A1 | 1/2012 | Behnke | |
| 2012/0075511 A1 | 3/2012 | Tay | |
| 2012/0227646 A1 | 9/2012 | Gelinske et al. | |
| 2012/0227647 A1 | 9/2012 | Gelinske et al. | |
| 2013/0053094 A1 | 2/2013 | Inagaki | |
| 2013/0211628 A1 | 8/2013 | Thurow et al. | |
| 2013/0317696 A1 * | 11/2013 | Koch | A01D 41/1272 701/33.1 |
| 2014/0019017 A1 | 1/2014 | Wilken | |
| 2014/0019018 A1 | 1/2014 | Baumgarten | |
| 2014/0053092 A1 | 2/2014 | Grevinga | |
| 2014/0053093 A1 | 2/2014 | Grevinga | |
| 2014/0129048 A1 | 5/2014 | Baumgarten | |
| 2014/0135082 A1 | 5/2014 | Batcheller | |
| 2014/0171161 A1 | 6/2014 | Bischoff | |
| 2014/0208708 A1 * | 7/2014 | Waechter | A01F 15/08 56/10.2 R |
| 2014/0298259 A1 | 10/2014 | Meegan et al. | |
| 2014/0315619 A1 | 10/2014 | Bowers et al. | |
| 2015/0009328 A1 | 1/2015 | Escher | |
| 2015/0046043 A1 | 2/2015 | Bollin et al. | |
| 2015/0293507 A1 | 10/2015 | Burns | |
| 2016/0000008 A1 | 1/2016 | Scholer et al. | |
| 2016/0029558 A1 | 2/2016 | Dybro et al. | |
| 2016/0052525 A1 | 2/2016 | Tuncer et al. | |
| 2016/0189007 A1 | 6/2016 | Wellington | |
| 2017/0160916 A1 | 6/2017 | Baumgarten et al. | |

FOREIGN PATENT DOCUMENTS

| | | |
|---|---|---|
| CA | 2334400 | 12/2006 |
| CN | 101887018 | 1/2012 |
| CN | 102498794 | 6/2012 |
| DE | 102014216593 | 2/2016 |

(56) References Cited

FOREIGN PATENT DOCUMENTS

| EP | 0826959 | 3/1998 |
|---|---|---|
| EP | 1221279 | 12/2001 |
| EP | 1095262 | 1/2003 |
| EP | 1956361 | 8/2008 |
| EP | 2123144 | 2/2012 |
| EP | 2036424 | 3/2013 |
| EP | 2687924 | 6/2013 |
| JP | 2002318198 | 10/2002 |
| JP | 2006201130 | 8/2006 |
| WO | 1983002872 | 9/1983 |
| WO | 1997042489 | 11/1997 |
| WO | 1999046971 | 9/1999 |
| WO | 2000000818 | 1/2000 |

OTHER PUBLICATIONS

Klassen, et al., "Investigation of a Feedrate Sensor for Combine Harvesters", SAE Technical Paper 932428, 1993, p. 1-8.
Kotyk, et al., "Control System for Combine Harvesters", WESCANEX '91 'IEEE Western Canada Conference on Computer, Power and Communications Systems in a Rural Environment', May 29-30, 1991, pp. 96-102.
Romeo, et al., "Camera Sensor Arrangement for Crop/Weed Detection Accuracy in Agronomic Images", Sensors, vol. 13, No. 4, Apr. 2, 2013, pp. 4348-4366.
Fu, et al., "Discriminant Absorption-Feature Learning for Material Classification", IEEE Transactions on Geoscience and Remote Sensing, vol. 49, No. 5, May 2011, pp. 1536-1556.
Gunasekaran, et al., "Soybean Seed Coat and Cotyledon Crack Detection by Image Processing", Journal of Agricultural Engineering Research, vol. 41 (1988), pp. 139-148.
Kinnikar, et al., "Identification and Detection of Seed Borne Diseases of Soybean Using Image Processing—A Survey", International Journal of Emerging Technology in Computer Science & Electronics (IJETCCSE), vol. 14, Issue 2, Apr. 2015, pp. 363-368.
"International Search Report and Written Opinion", PCT/US2015/050059, dated Dec. 10, 2015.
"Extended European Search Report", Appareo Systems, LLC, European Patent Application No. 15839749.7, dated Mar. 29, 2018.
"Extended European Search Report", Intelligent Agricultural Solutions LLC, European Application No. 15840433.5, dated Apr. 6, 20108.

* cited by examiner

Perspective View

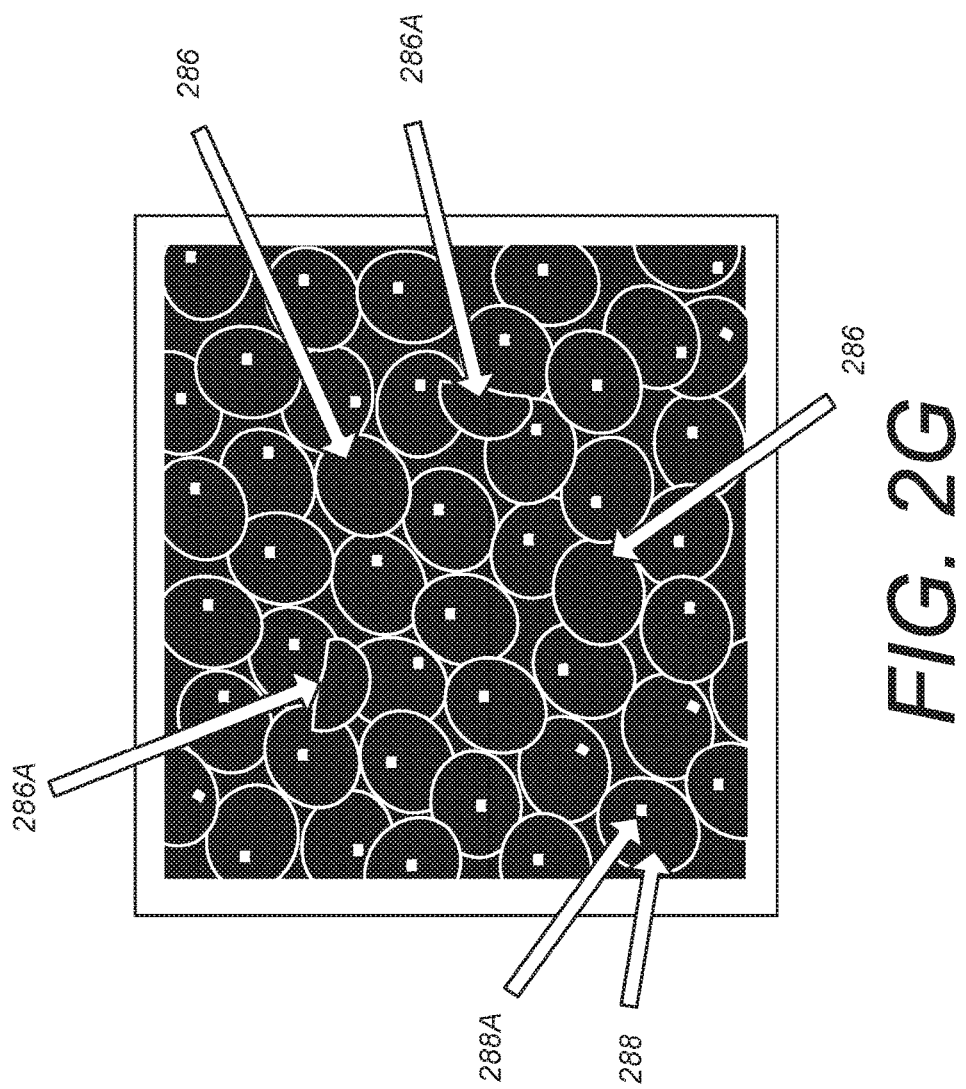

Clean Grain Auger
(not fully shown, see Fig. 1)
delivers harvested grain to
bottom of grain elevator 400

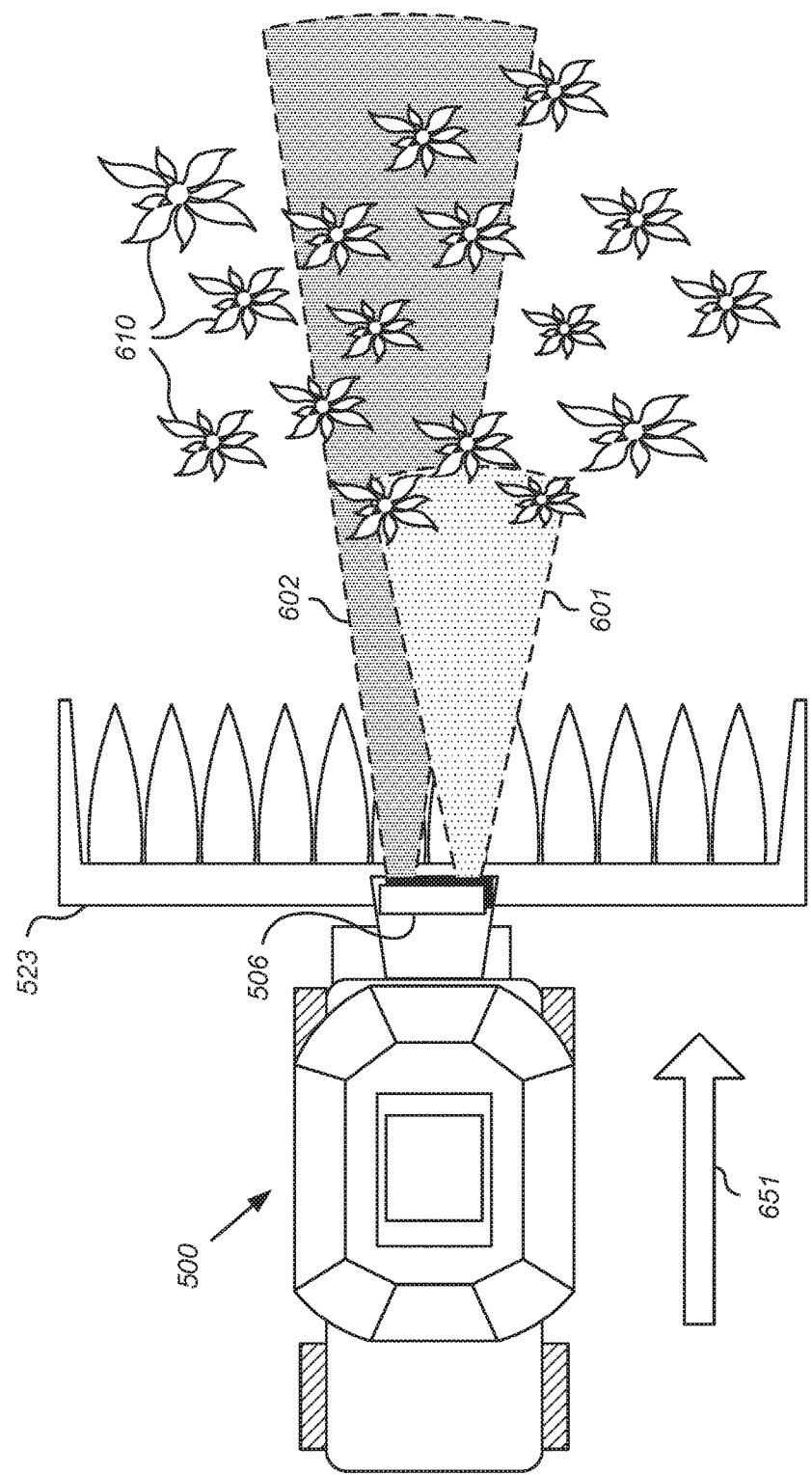

The curve of a line of light as it might appear displayed on an uneven wall of plants when viewed from the front.

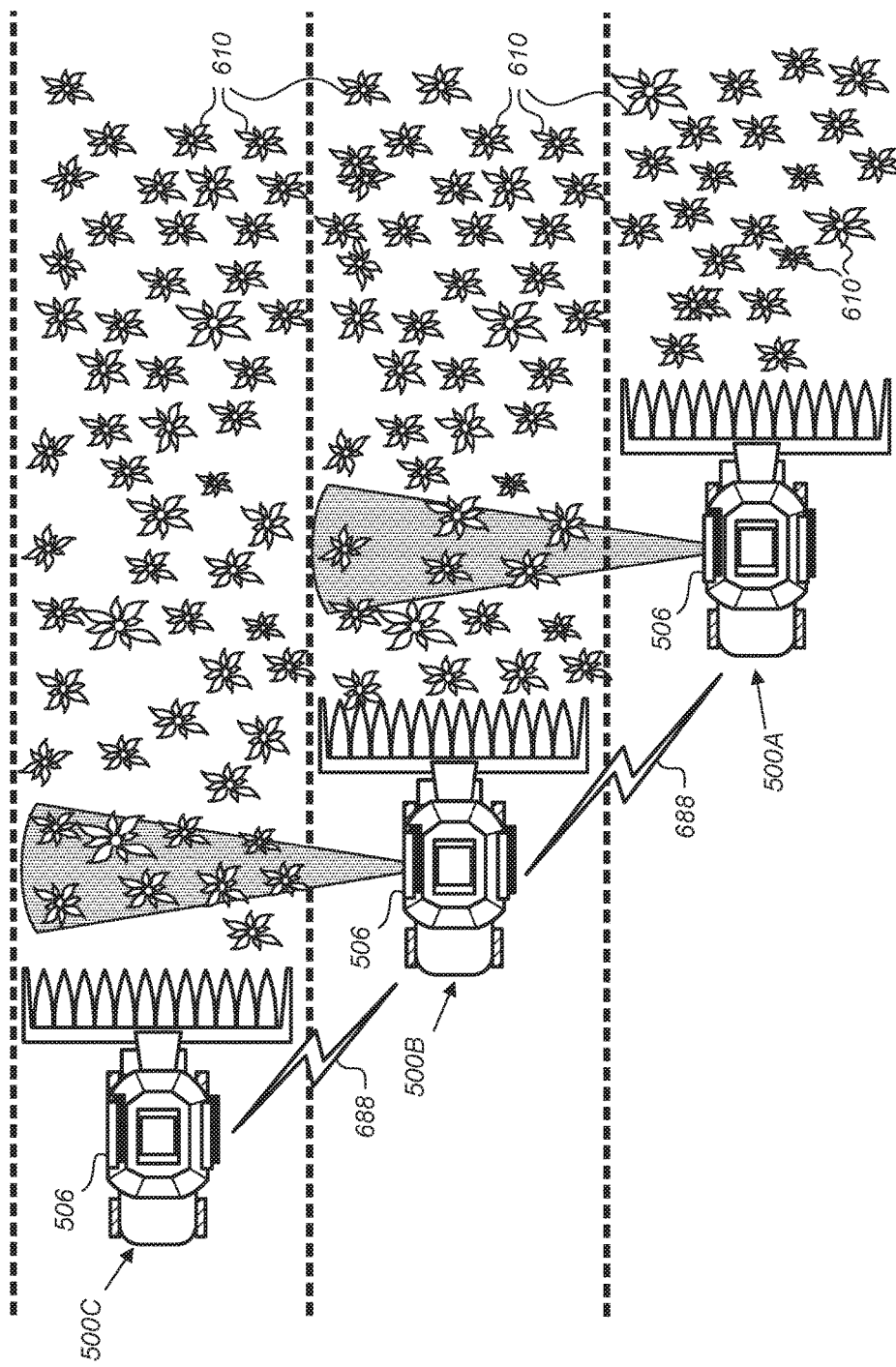

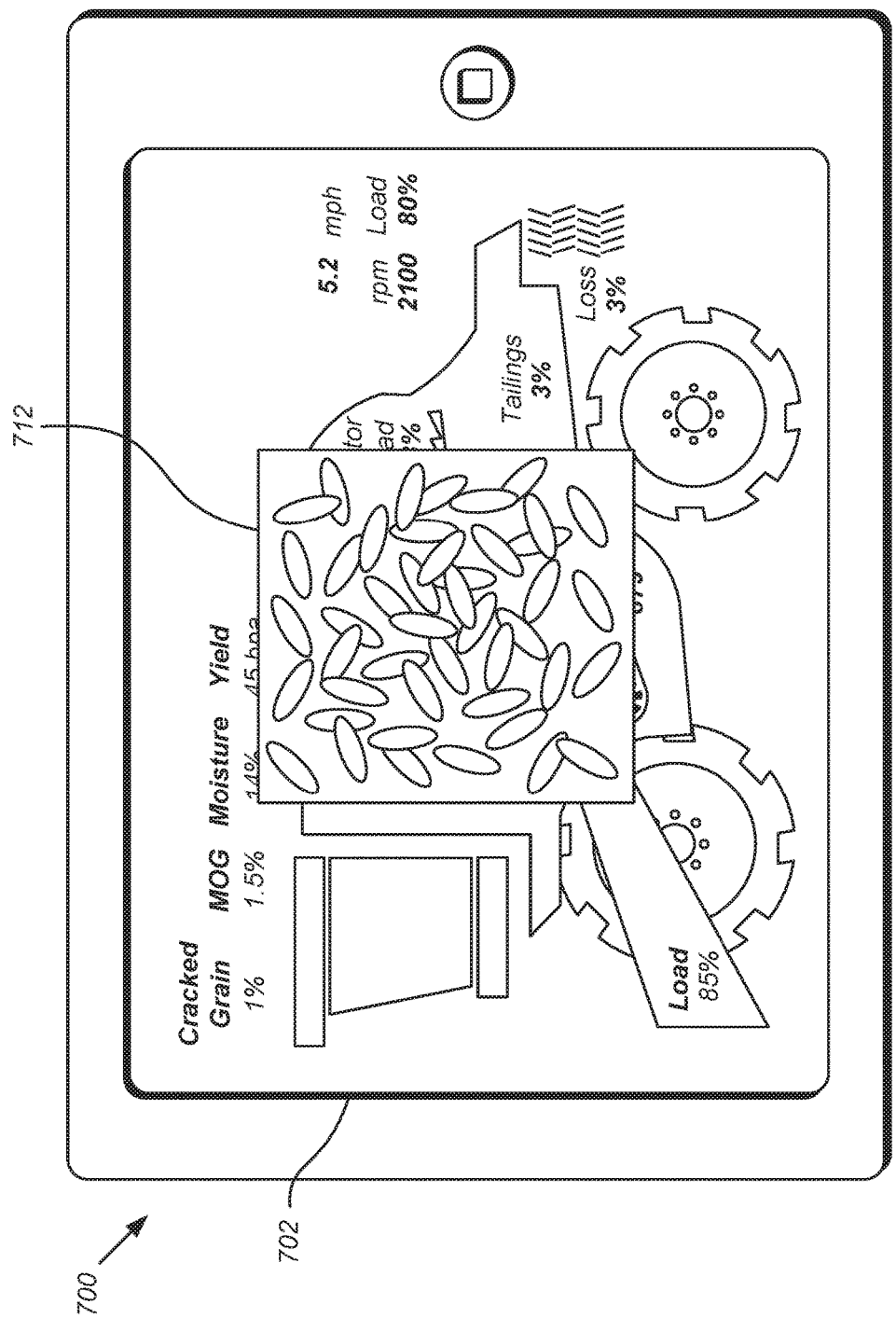

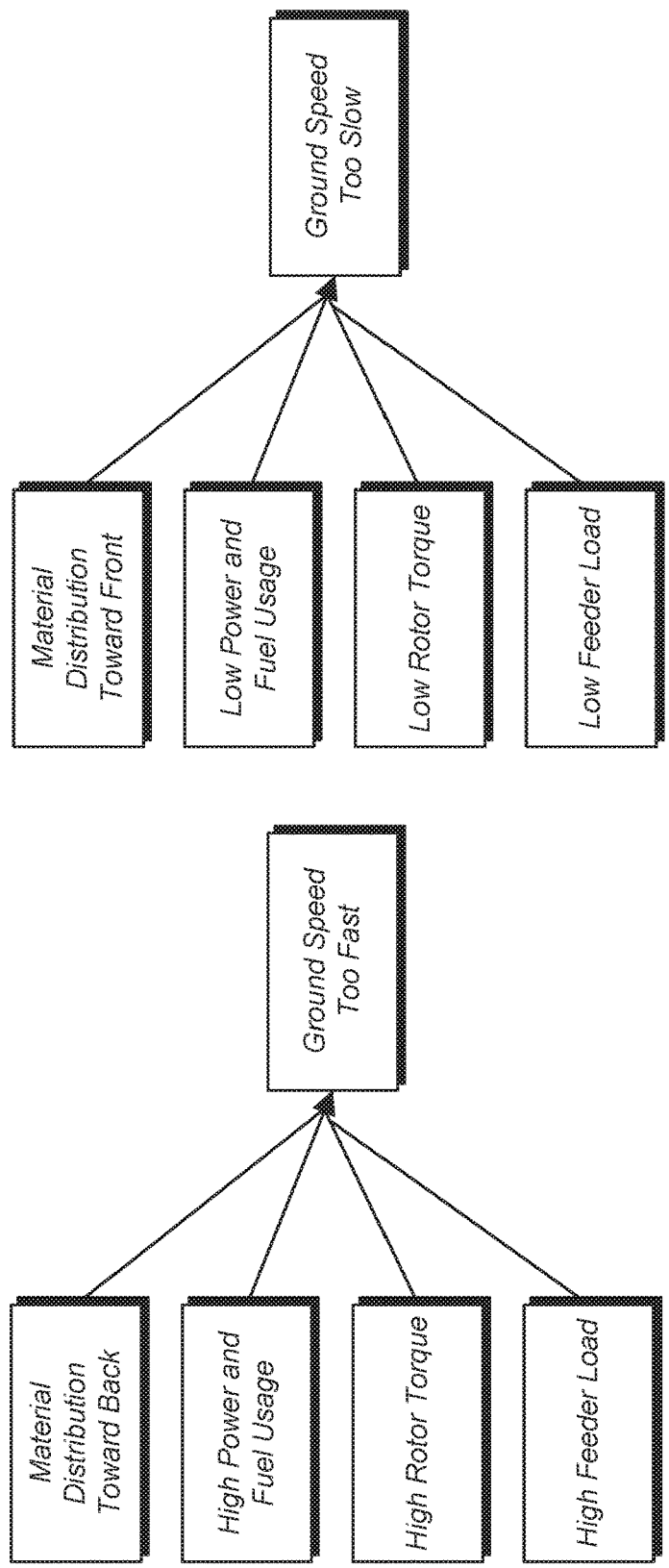

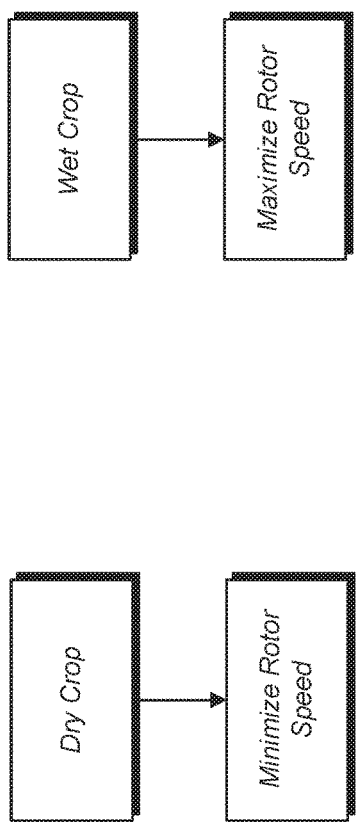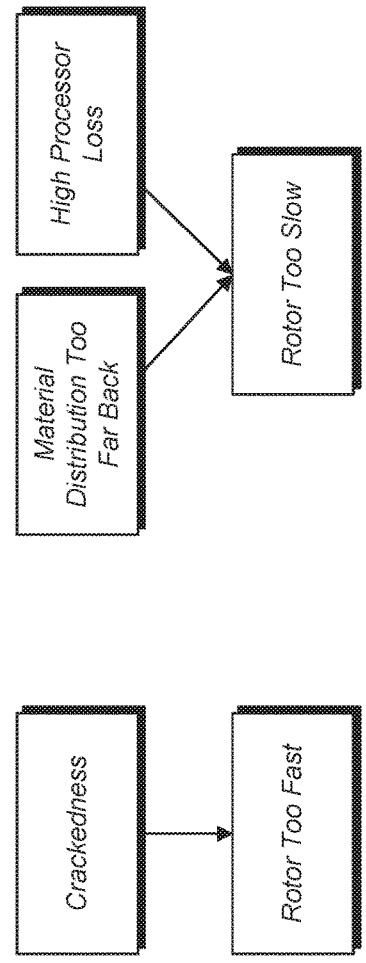

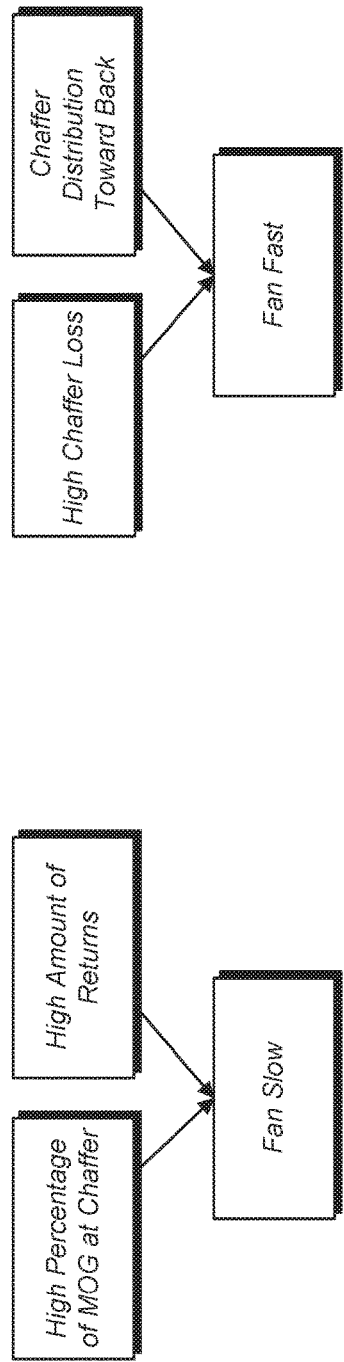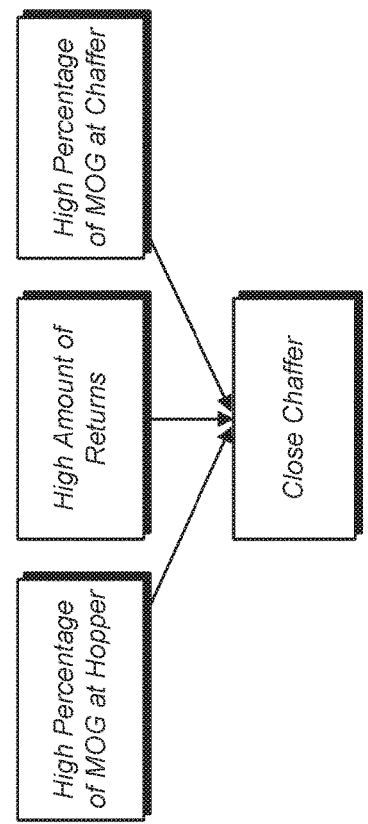
FIG. 10I
FIG. 10J
FIG. 10K

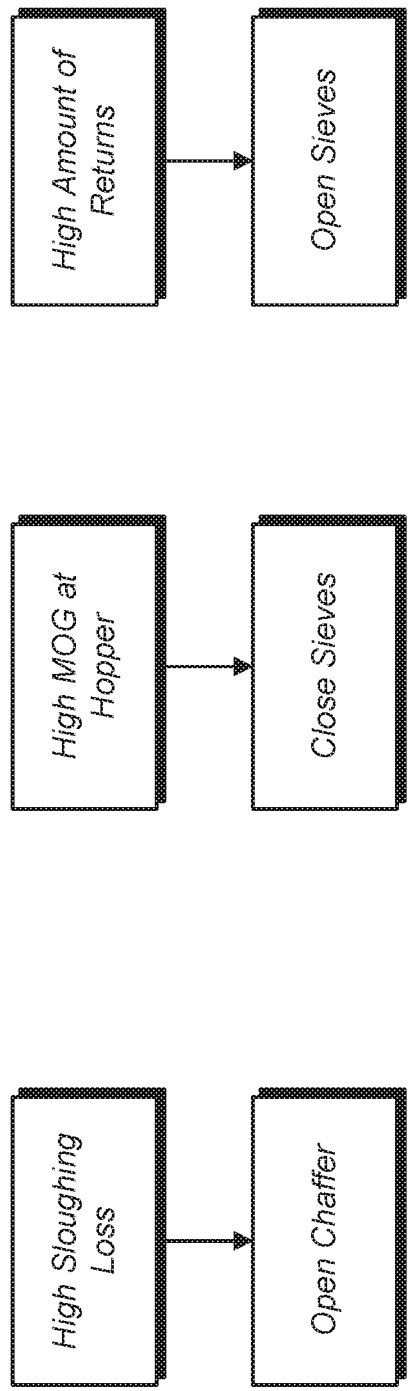

LOAD-BASED YIELD SENSOR

CROSS REFERENCE TO RELATED APPLICATION

This patent application claims the benefit of U.S. Provisional Application No. 62/049,616, filed Sep. 12, 2014 and entitled "METHOD AND SYSTEM FOR COMBINE AUTOMATION," which is incorporated by reference in its entirety.

BACKGROUND OF THE INVENTION

1. Field of the Invention

This invention relates generally to the field of precision agriculture, and specifically to a method and system of automating the set up and adjustment of a combine or similar agricultural vehicle.

2. Description of the Related Art

There is a desire to automate the adjustment of a combine (also known as a "harvester") so that very little human know-how is required to operate the vehicle. This would enable the hiring of unskilled labor to operate the combine, reducing the cost to the farmer. It could also increase the efficiency of the harvesting process, and therefore the crop yield and machine productivity.

Attempts have been made to automate combines already, but the sensors that have been used to sense the necessary conditions, such as load on the machine and the cleanliness of the crop being harvested, are inadequate for the job.

What is needed in the art is a method and system for automating a combine that relies on advanced sensors that can detect and monitor the amount and quality of material moving through the combine at any time.

SUMMARY OF THE INVENTION

This invention describes a method and system for the automatic adjustment of a combine, or for providing directives to an operator to do the same.

In one aspect of the invention, a harvesting machine capable of automatic adjustment is provided, comprising a plurality of material flow sensors, a control system, a processor, and software, wherein the material flow sensors are capable of sensing an amount of crop material passing by them, wherein the control system is capable of adjusting a set of internal elements of the harvesting machine, wherein the software is hosted on the processor, wherein the processor is operatively coupled to the control system and the plurality of material flow sensors, wherein the software uses information sensed by the plurality of material flow sensors to determine if the set of internal elements of the harvesting machine are set for optimal machine performance, and wherein the software sends commands to the set of internal elements of the harvesting machine in order to improve the machine performance.

In another aspect of the invention, a material flow sensor is provided, comprising an acoustic chamber, an impact plate and a housing, a pneumatic impulse line, a microphone, and an electronics module, wherein the acoustic chamber and the microphone are connected by the pneumatic impulse line, wherein the housing is shaped so as to direct sound waves created by at least one object striking the impact plate into the pneumatic impulse line, wherein the sound waves move through the pneumatic impulse line into the microphone, wherein the microphone detects the sound waves and converts them into an electrical signal, wherein the microphone is electrically connected to the electronics module, and wherein the electronics module analyzes the electrical signal and converts it into a representative mass of the at least one object striking the impact plate.

In yet another aspect of the invention, a grain quality sensor is provided, comprising a lens, a filter, a photosite array, at least one illumination source, and an electronics module, wherein the filter is placed between the lens and the photosite array, wherein the illumination source directs light containing a known set of wavelengths onto a crop sample, wherein the lens picks up any light reflected by the crop sample and directs it into the filter, wherein the filter allows light to pass into different parts of the photosite array such that certain locations on the photosite array only get certain frequencies of the reflected light and other certain locations on the photosite array only get other certain frequencies of the reflected light, wherein the electronics module is electrically connected to the photosite array and capable of determining which parts of the photosite array received light and what frequency the light received was, wherein the electronics module can analyze the optical data received by the photosite array, wherein the analysis of the optical data is used to determine the composition of different parts of the crop sample, and wherein no image of the crop sample is ever created.

In yet another aspect of the invention, a method of creating images which contain only a portion of the photographed subject matter is provided, the method comprising the steps of placing a color filter on a photosite array, focusing light on the color filter, capturing photons in a photosite array, analyzing and processing the information gathered on the photons captured, determining the color information represented by individual photosites in the photosite array, altering the color information so as to delete information from photosites representing colors of a certain frequency, and creating an image from the remaining color information, wherein an image can be created that contains only some of the original elements present in the photographed subject matter.

In yet another aspect of the invention, a crop quality sensor is provided, comprising an illumination source, an imaging device, a processor; and software executing on the processor, wherein the illumination source is shone onto a crop sample, wherein the crop sample is such that individual kernels of the crop have a shiny outer casing and a dull inner surface when broken open, wherein an image is taken with the imaging device of the illuminated crop sample, wherein the software is executing on the processor, wherein the software is used to analyze the image to identify the outlines of individual kernels and to identify which of those outlines contain a specular highlight, and wherein the presence of a specular highlight within an outline is indicative that that kernel is whole and unbroken and the absence of such a specular highlight is indicative of a broken kernel.

In yet another aspect of the invention, a yield sensor is provided, comprising an acoustic chamber comprising an impact plate and a housing, a pneumatic impulse line, a microphone, and an electronics module, wherein the acoustic chamber and the microphone are connected by the pneumatic impulse line, wherein the housing is shaped so as to direct sound waves created by at least one object striking the impact plate into the pneumatic impulse line, wherein the sound waves move through the pneumatic impulse line into the microphone, wherein the microphone detects the sound waves and converts them into an electrical signal, wherein the microphone is electrically connected to the electronics module, and wherein the electronics module analyzes the electrical signal and converts it into a representative mass of the at least one object striking the impact plate.

In yet another aspect of the invention, a crop mass predictive sensor is provided, comprising an imaging device, a LIDAR, a first radar emitting a frequency of energy that is absorbed by plant mass, and a second radar emitting a frequency of energy that passes through plant mass without being absorbed, wherein the imaging device, LIDAR, first radar, and second radar are focused on the crop material in front of an agricultural vehicle, and the information gathered from each of these components is used to calculate an estimated mass for the crop material that is about to enter the agricultural vehicle.

In yet another aspect of the invention, a crop mass predictive sensor is provided, comprising an imaging device, a LIDAR, a first radar emitting a frequency of energy that is absorbed by plant mass, a second radar emitting a frequency of energy that passes through plant mass without being absorbed, and a location sensor, wherein the imaging device, LIDAR, first radar, and second radar are focused on the crop material to the side of an agricultural vehicle, and the information gathered from each of these components is used to calculate an estimated mass for the crop material, and the estimated mass is stored along with a current location from the location sensor for subsequent use, by the current machine, or transmitted to a separate machine for its use.

In yet another aspect of the invention, a method of determining the shape of at least a portion of a surface relative to a designated external point of reference is provided, comprising the steps of placing an imaging device at the designated external point of reference such that it can take an image of the at least a portion of a surface, projecting a straight line onto the at least a portion of a surface from a point that is offset by a predetermined angle from the designated external point of reference, taking an image of the at least a portion of a surface with the imaging device, and analyzing the image to determine the shape of the at least a portion of a surface, wherein the analysis comprises determining the apparent distance from the imaging device to a series of points along the projected line based on the perceived shape of the line when viewed from the designated external point of reference.

In yet another aspect of the invention, a mobile device for use as a user interface for an agricultural vehicle is provided, wherein the mobile device can receive messages from and transmit messages to the control system of the agricultural machine.

In yet another aspect of the invention, a harvesting machine capable of providing recommendations to an operator comprising a plurality of material flow sensors; a control system, a display, a processor, and software, wherein the material flow sensors are capable of sensing an amount of crop material passing by them, wherein the control system is capable of adjusting a set of internal elements of the harvesting machine, wherein the software is hosted on the processor, wherein the processor is operatively coupled to the control system and the plurality of material flow sensors, wherein the software uses information sensed by the plurality of material flow sensors to determine if the set of internal elements of the harvesting machine are set for optimal machine performance, and wherein the software sends recommended control settings to the display, whereby the operator uses the recommended control settings as necessary to change the settings on the harvesting machine's internal elements for optimal performance.

In yet another aspect of the invention, a method of estimating the amount of crop mass entering a harvesting machine is provided, comprising the steps of attaching potentiometers to the front feed roller of a the harvesting machine and using the potentiometers to measure the magnitude of deflection of the front feed roller as crop mass is pushed under the front feed roller, causing it to rise.

In yet another aspect of the invention, a method of estimating the mass of crop entering into a grain tank from a clean grain elevator on a harvesting machine is provided, comprising the steps of mounting at least one load sensor on an upper bearings of a conveyor belt moving grain through the clean grain elevator into the grain tank, using the load sensors to measure the load on the conveyor belt when no grain is present in the clean grain elevator, using the load sensors to measure the load on the conveyor belt when grain is moving through the clean grain elevator, and comparing the load with no grain present to the load when grain is present to determine the mass of crop moving through the clean grain elevator.

The features, functions, and advantages can be achieved independently in various embodiments of the present invention or may be combined in yet other embodiments in which further details can be seen with reference to the following description and drawings.

BRIEF DESCRIPTION OF THE DRAWINGS

The drawings constitute a part of this specification and include exemplary embodiments of the invention illustrating various objects and features thereof, wherein like references are generally numbered alike in the several views.

FIG. 2G shows an image that has been processed to highlight "bright" spots or specular highlights.

FIG. 6A shows a top view of a combine showing how the radar-based components of the look-ahead sensor of FIG. 5 would work to predict incoming crop load.

FIGS. 6D through 6J illustrate an alternate embodiment of the LIDAR portion of the crop mass sensor 506.

FIG. 7C shows yet another embodiment of an application user interface page for the present invention as displayed on a mobile computing device.

DETAILED DESCRIPTION OF THE PREFERRED EMBODIMENTS

I. Introduction and Environment

Figure 1:
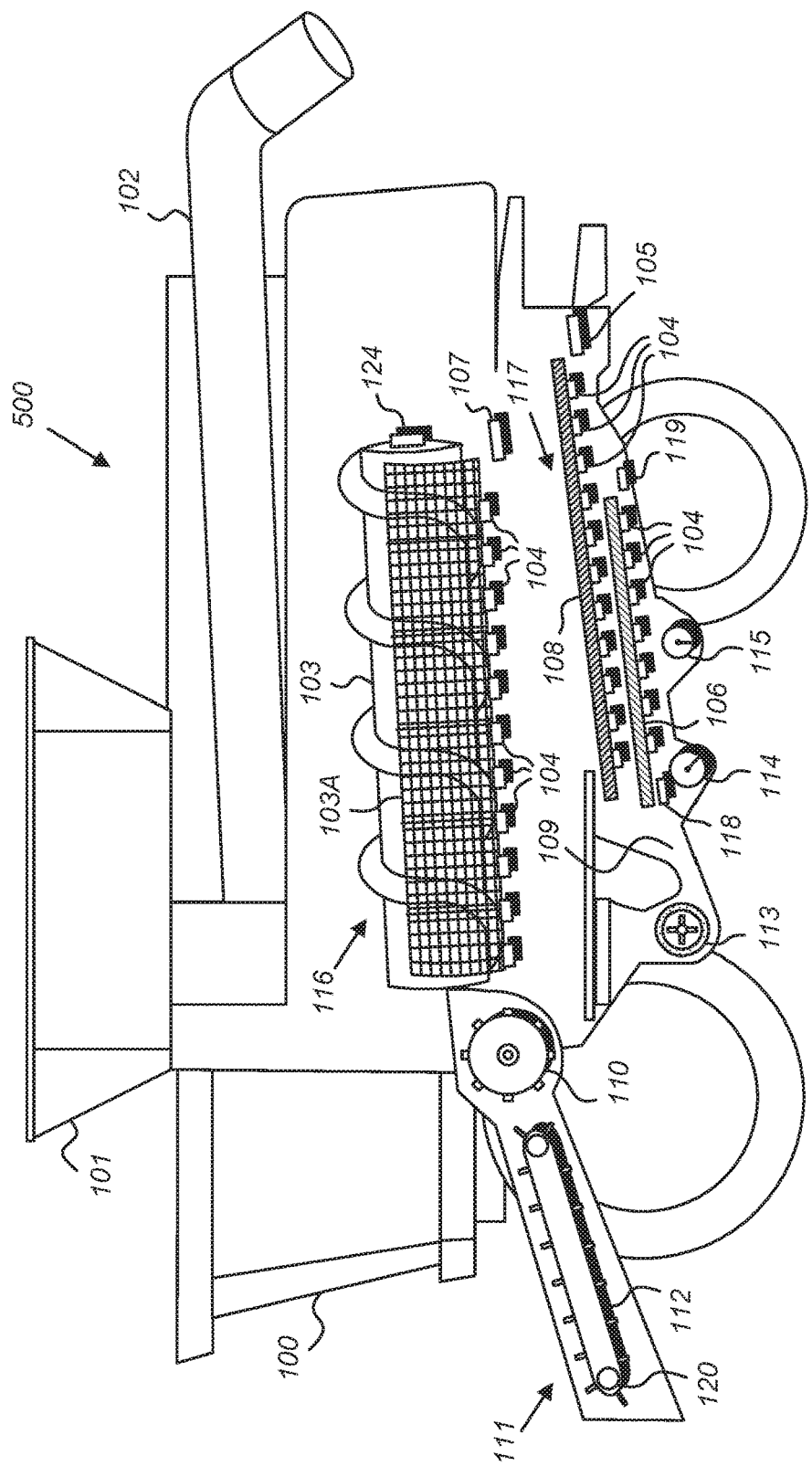
FIG. 1 is a block diagram of a combine showing the various components of the combine involved in the present invention, along with the placement of sensors needed for the present invention.

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Said terminology will include the words specifically mentioned, derivatives thereof and words of similar meaning.

With reference now to the drawings, and in particular to FIGS. 1 through 10N thereof, a new method and system of automating the adjustment of a combine embodying the principles and concepts of the present invention will be described.

In general terms, the present invention will automate the adjustment of a combine by following a series of steps, including:

A. Equipping an agricultural combine with new sensors placed throughout the combine to sense the state of the material flowing through the machine at any given time and location internal to the machine.

B. Collecting and analyzing the data gathered on the material flow.

C. Determine which adjustments could be made to internal components of the combine (based on the analysis of the data collected from the sensors) to optimize the combine's performance.

D. Automatically make the adjustments to the combine components to optimize the combine's performance, OR E. Make recommendations to the operator of the combine, or provide them with actionable data, so that they may make manual adjustments to the combine components to optimize the combine's performance.

FIGS. 1 through 6C describe the types of sensors used to complete Steps A and B of the above process. FIGS. 8 through 10N describe the steps needed to complete Steps C through E of the above process. FIGS. 7A through 7C describe the invention's optional user interface which can be used to make the recommendations to the operator as discussed in Step E of the above process.

II. Crop Material Flow Sensor Type and Placement

The key to the present invention is to be able to detect the status of the machine (the combine) at any given point, especially to have detailed information on the flow of crop material through the combine system and the condition of the crop material.

At optimal/ideal performance, the crop material collected (harvested) by a combine would be as close to 100% "clean grain" (the "grain" is the seeds of the crop being harvested) as possible with little to no cracked grain (grain that has been damaged, sometimes by the harvesting process itself) and little to no "material other than grain," often referred to by those skilled in the art as MOG. Like the phrase "material other than grain" implies, MOG is any material that is moved through the combine during harvesting that is not grain. MOG may include things like rocks, dirt, trash, straw and chaff (plant matter that is something other than the grain, such as the dry protective casings of seeds and grains, parts of the stems, flowers, leaves, etc.

Improper settings of internal components of a combine harvesting machine can result in an increase in cracked grain and/or MOG, which lowers the value of the harvested crop by adding weight and volume to the harvested crop without adding additional value, or by otherwise reducing the quality of the grain. Improper settings can also result in clean grain being lost out the back of the combine, reducing yield.

For instance, the crop being harvested is collected by the combine and fed toward a spinning cylinder (called a "rotor") which spins the material against one or more curved metal gratings (called "concaves"). The concaves are shaped to match the curve of the rotor and can be moved farther and closer to the rotor as needed. As the rotor carries the crop material past the concaves, the crop material is threshed as it is moved over and impacts the concaves, knocking the seeds (the grain) loose from the rest of the plant. The spacing between the rotor and concave can be adjusted based on the crop type and the size of the grain being harvested (and other factors, such as crop load). If the concave is too close to the rotor, however, or if the rotor speed is too fast, the grain can be damaged and cracked, which makes it more likely to be lost in the harvesting process (more likely to be blown away with the chaff in the harvesting process) and also introduces problems in handling and storage of the grain, including harboring insects and increasing mold growth, as well as reducing the quality of the grain (for example, reducing protein content). Having the concave too close to the rotor can also over-thresh the grain, increasing the amount of MOG in the grain that passes through the concaves.

Therefore, if there was a way to detect the percentage of cracked grain that winds up in the clean grain tank during harvesting, then it would be possible to correct the rotor speed or the rotor-to-concave spacing in real time, during the harvesting process, to minimize the percentage of cracked grain.

This is just one example of a combine adjustment that can be made as part of the present invention. Other examples will become evident throughout the remainder of this specification.

Turning now to FIG. 1, we will discuss the components of a combine 500 in additional detail, as well as the various types of sensors that can be added to the combine 500 in order to implement the present invention. A combine 500, also known as a combine harvester, or simply a harvester, is an agricultural machine that cuts, threshes, and cleans a grain crop in a single machine (in a single operation). It is typically self-propelled (a vehicle and not an implement) that is driven into and through a crop at harvest time. The operation and working components of a traditional combine 500 are well known in the prior art and this specification will not address all elements of a combine, but will address those which are new and/or important to the operation of the present invention.

In FIG. 1, a combine 500 has a cab 100 where the operator of the vehicle is housed, and the cab 100 is typically located on what is considered to be the front of the combine 500 (the direction of forward travel). At the very front of a combine 500, a removable header 523 (see FIGS. 6A-6C, header not included in FIG. 1) pushes into the crop in the direction of forward travel and cuts the crop and pulls it into the feeder housing 111. A typical header 523 has a reciprocating knife cutter bar for cutting the plants near the ground and a revolving reel to cause the cut crop to fall back into the feeder housing 111. Other versions of combines may use a "pick-up header" instead of a cutting header for crops that are cut by a separate machine and placed into windrows that are later picked up by the combine with such a header. The type of header is not pertinent to the present invention, and the example shown herein should not be considered limiting. The feeder housing 111 contains a conveyor chain 112 or similar mechanism to pull the cut crop up into the combine for threshing.

One of the important pieces of information for a self-adjusting combine is to know the load seen on the conveyor chain 112, as early as possible in the harvesting process, as crop moves into the feeder housing 111. Therefore, one or more potentiometers 120 are mounted on the front feed roller to measure the amount of deflection seen at this location. The material pushing into the feeder housing 111 will actually push up on the conveyor chain 112 mechanism, which "floats" up and down as the amount of material changes. The conveyor chain 112 mechanism typically can detect when one side of the feeder housing 111 has more material than the other, as both sides of the conveyor chain 112 float separately and therefore the separate sides are deflected upward based on the amount of material under each side, and the deflection can be translated into amount of mass, or load. In the typical embodiment, there is at least one potentiometer per side on the conveyor chain 112 mechanism, such that the deflection of each side can be measured independently.

This information can be digitized and sent to other locations on the combine 500 for use in combine adjustment (as well as other functions).

The crop material is delivered by the conveyor chain 112 to the feed accelerator 110, which is a rotating drum covered in paddles that pulls the crop material up into the machine, delivering it into the threshing assembly 116. The threshing assembly 116 includes a rotor 103 and one or more concaves 103A. The rotor 103 is a spinning cylinder with projections, such as paddles (also known as threshing elements), arranged in the shape of the inclined plane of an auger, on it such that is will push the crop material through the combine from the front end of the rotor 103 to the back end of the rotor 103. The crop material is pulled through the threshing assembly 116 by the spinning motion of the rotor 103, and, as it moves from front to back, the crop material is dragged across the concaves 103A, causing the crop material to be threshed. The concaves 103A are metal gratings with holes through which threshed grain (the seeds that are pulled or shaken off of the crop material) may drop. The material that passes through the concaves 103A drop into the cleaning shoe 117, where the crop material is further processed to separate the clean grain from the chaff before it is collected.

In the embodiment shown in FIG. 1, a series of crop material sensors 104 are placed on the bottom side of the concaves 103A. These crop material sensors 104 can detect the amount of material dropping on them and can, in the preferred embodiment, distinguish between grain and MOG. These crop material sensors 104 may be any type of appropriate sensor for detecting the impact of particles, including piezoelectric sensors, optical sensors, and mechanical sensors, but in the preferred embodiment are acoustic sensors which can detect the sound of material impacting the sensors and ideally distinguish between the heavier sounds of grain hitting the sensor and the lighter sounds of chaff hitting the sensors.

It is helpful to know the load on the rotor 103 in order to properly adjust the combine settings. The "rotor load" is the measure of the pressure put on the rotor 103, and one method of measuring this rotor load is to place a sensor on the rotor pulley actuator 124 which can measure the differences in load as the rotor pulley spins the rotor. The rotor load is calculated based on load on the rotor pulley actuator 124 and communicated to the combine system to use in determining the combine settings.

After the crop material passes through the rotor 103 and the concaves 103A, it falls down into the cleaning shoe 117. The cleaning shoe 117 typically includes a chaffer 108 and a sieve 106. The chaffer 108 and the sieve 106 are "filters" that typically have adjustable-size openings in them and which further aid in the separation of grain from MOG. The chaffer 108 typically has larger openings than the sieve 106, and so the chaffer 108 will allow larger pieces of crop material to pass through to the sieve 106. As the crop material falls on the chaffer 108 and sieve 106, further separation of the material occurs. Forced air generated by one or more fans 113 is propelled through channel 109 and directed up through the chaffer 108 and the sieve 106. The air will carry lighter material such as chaff up and out of the back of the combine 500 to be dispersed on the ground.

A rotor loss sensor 107 will detect the amount of material that falls from the back of the rotor (meaning it was not completely threshed as it traveled along the rotor). This rotor loss sensor 107 may be any appropriate sensor that detects the impact of crop material, and which can, in the preferred embodiment, distinguish between grain and MOG. The rotor loss sensor 107 may be any type of appropriate sensor for detecting the impact of particles, including piezoelectric sensors, optical sensors, and mechanical sensors, but in the preferred embodiment is an acoustic sensor which can detect the sound of material impacting the sensors at a minimum and, ideally, distinguish between the heavier sounds of grain hitting the sensor and the lighter sounds of chaff hitting the sensors.

At the back end of the chaffer 108 is a grain loss sensor 105. In the preferred embodiment, the grain loss sensor 105 is a sensor using acoustic sensor technology, which can detect the sound of material impacting the sensor and ideally distinguish between the heavier sounds of grain hitting the sensor and the lighter sounds of chaff hitting the sensors. The purpose of the grain loss sensor 105 is to detect the amount of clean grain that is being lost out of the back of the combine 500.

At the back end of the sieve 106 is a tailings sensor 119. In the preferred embodiment, the tailings sensor 119 is a sensor using acoustic sensor technology, which can detect the sound of material impacting the sensor and ideally distinguish between the heavier sounds of grain hitting the sensor and the lighter sounds of chaff hitting the sensors. The purpose of the tailings sensor 119 is to detect the amount of tailings that falls out of the back of the cleaning shoe 117. In harvesting, "tailings" are a mixture of grain and the mature vegetation on which the grain grows, and, with respect to the combine, the tailings represent the crop material that falls out the back of the cleaning shoe 117. In a typical combine, the tailings will be given a "second chance", where they are collected by a tailings auger 115, which delivers the tailings to a tailing elevator (not shown in drawing) to be transported back to the rotor 103 for another attempt at threshing.

The heavier grain that is successfully threshed after traveling through the rotor 103 and concaves 103A and the cleaning shoe 117 will fall off the front end of the sieve 106 rather than being blown back by the air coming from the fan 113. The grain falling off the front end of the sieve 106 will impact a clean grain sensor 118. In the preferred embodiment, the clean grain sensor 118 is a sensor using acoustic sensor technology, which can detect the sound of material impacting the sensor and ideally distinguish between the heavier sounds of grain hitting the sensor and the lighter sounds of chaff hitting the sensors.

After impacting the clean grain sensor 118, the clean grain will drop into the clean grain auger 114 and be transported to a clean grain elevator 400 (not shown in this figure but presented in FIG. 4) where it is delivered to the grain tank 101.

Eventually, the grain captured in the grain tank 101 will be offloaded to an agricultural cart or vehicle. This offloading is done through the offload auger 102.

It should be noted that sensors 104, 105, 107, 118, and 119, are intended to be acoustic material flow sensors in the preferred embodiment, similar to the energy sensing acoustic technology (ESAT) sensors manufactured by Appareo systems, including those disclosed in WO/2012/125575, the latter publication incorporated herein by reference in its entirety, or variants thereof.

An acoustic material flow sensor for a harvesting machine might comprise an acoustic chamber with an impact plate and a housing, a pneumatic impulse line, a microphone, and an electronics module. The housing of the acoustic material flow sensor is shaped so as to direct sound waves created by crop matter that is striking the impact plate into a pneumatic impulse line connected to the chamber. Once the sound waves enter the pneumatic impulse line, they travel down the line into a microphone connected to the other end of the pneumatic impulse line.

The microphone then detects the sound waves and converts them into an electrical signal that is a representation of a "sound power" derived from the energy of the sound waves collected. The electronics module analyzes the electrical signal and converts it into a representative mass of the crop matter striking the impact plate. This may be done by a specialized audio processor, designed specifically for the analysis of audio signals, such as a processing chip designed for use in music-related applications.

The acoustic material flow sensor may also be able to analyze the frequencies of the sounds generated by crop matter striking the impact plate, and determine if material of largely different densities is striking the plate. Crop matter that is moving through a harvesting machine often contains "material other than grain", or MOG, which may be rocks, soil, plant matter other than seed, etc. By distinguishing between sound waves representing different densities of crop matter, an approximate percentage of MOG contained in the crop matter can be determined.

However, these material flow sensors may comprise sensors of a variety of different structures and/or types, as would be known by one skilled in the art.

The purpose of FIG. 1 is to identify the various components of a combine and the variety of sensors needed to detect material flow through the combine at various points. Some of these sensors already exist in the prior art to collect information for use in other subsystems of a combine, and other sensors are new to the art and these new-to-the-art sensors will be described in additional detail in the remaining figures of this specification.

It should be noted that FIG. 1 represents one possible embodiment of a combine and is not intended to be limiting. For example, some combines place the rotor such that it is perpendicular to the direction of travel, rather than parallel to it. Some of the sensors described herein may be omitted without differing from the intent of the present application.

In addition to the sensors described in the previous section and as shown on FIG. 1, there are additional sensors that sense items other than the flow of material through the interior of the combine. These sensors, described in the following sections, include a grain quality sensor, a look-ahead crop mass sensor, a yield sensor, and a moisture sensor.

III. Grain Quality Sensor

The following section, including the discussion of FIGS. 2B through 4, presents a novel grain quality sensor for use in gathering data needed for the combine automation system and method. FIG. 2A shows a block diagram of a camera or "imaging device" from the prior art and how it is used to capture an image.

The concept behind a grain quality sensor is to somehow examine a sample of crop material from the clean grain tank of a harvester such as that shown in 101 on FIG. 1 to determine the percentage of (1) damaged grain, (2) material other than grain, and (3) clean grain. Damaged grain is grain or seeds of a crop for which the outer casing has been damaged, exposing the endosperm (the inside of the seed). Grain can be damaged by the harvesting process itself if the adjustments on the combine are not optimized. For instance, if the distance from the rotor to the concave gratings is too close, the grain can be caught between rotor and concave and threshed too "violently", causing damage to the outer casing of the grain/seed. Material other than grain, or MOG, as has been previously explained, is any plant material other than the seed, and can also include foreign matter such as rocks, soil, and other plant matter (such as weeds). Clean grain consists of undamaged grain/seed and no MOG.

By determining the percentages of damaged grain, MOG, and clean grain in a sample of harvested material, a control system for a combine can work to make automated adjustments to internal settings such as the distance from rotor to concave to improve the percentages of clean grain.

One way to analyze a grain sample to determine these percentages is to do it by image analysis. Several inventions in the prior art use a digital camera to take an image of a sample of grain and then analyze that image to search for cracked grain and MOG.

Figure 2A:
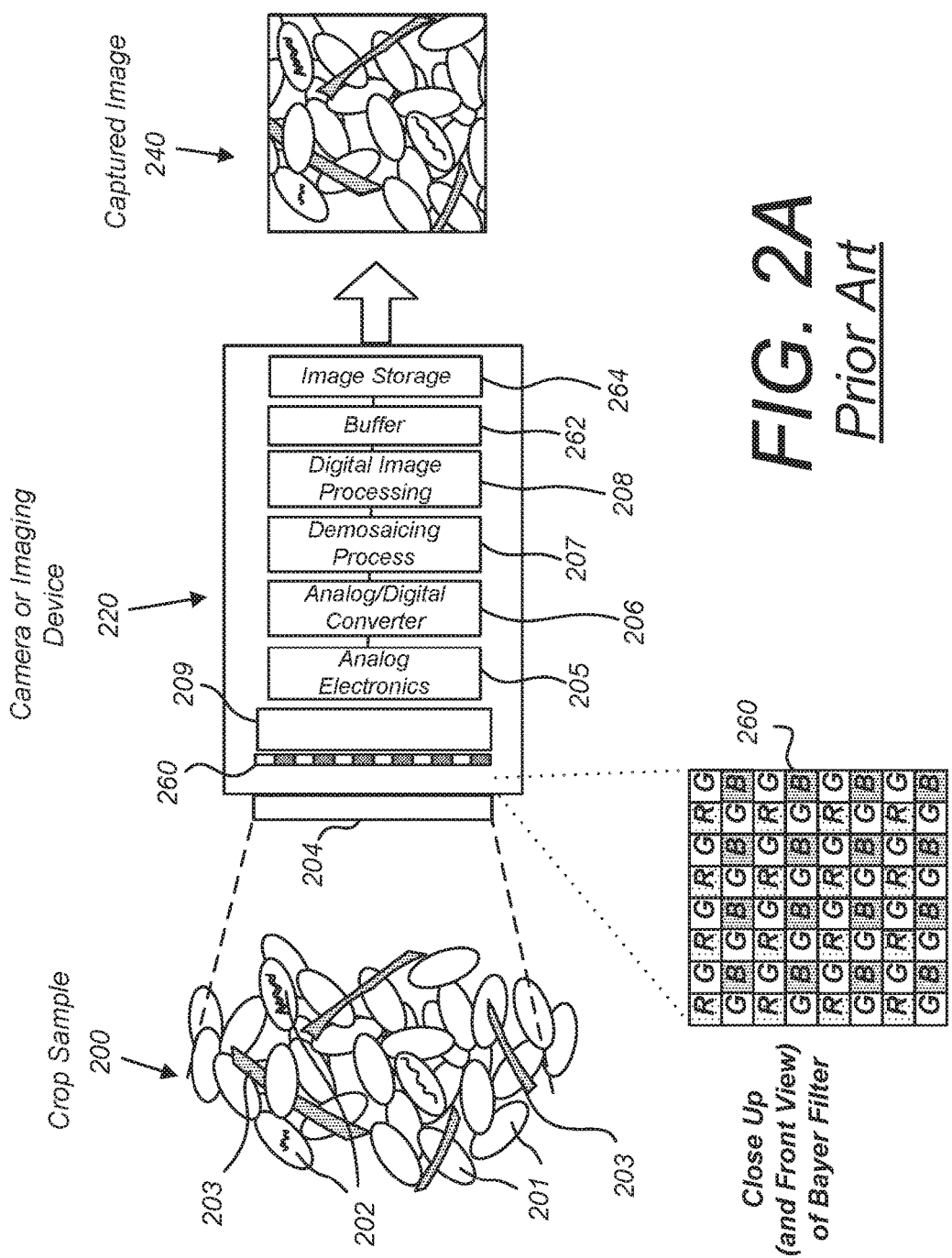
FIG. 2A shows a block diagram of a camera or "imaging device" from the prior art and how it is used to capture an image.

FIG. 2A shows a block diagram of a camera or "imaging device" from the prior art and shows how it is used to capture an image for analysis. A crop sample 200 contains a combination of clean grain 201, damaged grain 202, and MOG 203. Prior art inventions use a camera or similar imaging device 220 to capture an image 240 of the crop sample 200. The imaging device 220 comprises a lens 204, a color filter 260, a photosite array 209, and a series of functional blocks which are a mix of electronic hardware and firmware. There is a set of analog electronics 205 for powering and reading the photosite array 209, an analog to digital converter 206 for converting the analog voltage values read from the analog electronics 205 into digital values, a "demosaicing" process 207 which is required to compensate for the introduction of the color filter 260 (needed to produce an image with accurate color reproduction), digital image processing circuitry 208 required to perform the intensive amount of processing required to create a digital image, a memory buffer 262 to store the digital data as it is being assembled into a finished digital image, and finally image storage 264 to hold and maintain the final captured image 240.

The photosite array 209 consists of millions of tiny light cavities ("photosites") which can be uncovered to collect and store the photons of light reflected by an object or scene. Once the photosites have collected photons, the camera closes each of the photosites and then determines how many photons were collected by each. The relative quantity of photons in each cavity are then sorted into various intensity levels, whose precision is determined by bit depth (for example, 0-255 for an 8-bit image, or any other appropriate implementation).

However, the intensity levels calculated by the photosite array by themselves would only create grayscale (black and white) images, since these photosite cavities are unable to distinguish how many photons of each color they received. In order to capture color values of something, a filter 260 has to be placed over each cavity that permits only particular colors of light. A close-up view of one common type of filter 260 is shown in FIG. 2A. Most current digital cameras can only capture one of three primary colors in each cavity, and so approximately ⅔ of the incoming light is captured by a photosite array 209 with a color filter 260 on the front.

As a result, a digital camera 220 has to approximate the other two primary colors in order to have full color at every photosite. A typical way of doing this is to have the camera 220 look at the neighboring photosites to see how much of the other color was received there, and then interpolate a value for the current location. For instance, if a photosite with a red filter only collects photons of red light, then that same photosite can look at the number of photons received by the neighboring or nearby blue photosites to determine the approximate blue value to use for the red photosite location. Something similar is done for the green value at the photosite. In other words, in order to create an accurate image 240, steps must be taken to counteract the effects introduced by the filter 260.

The most common type of color filter is called a "Bayer array," and this arrangement of filter colors is shown in the close up of the filter 209 shown in FIG. 2A. This arrangement has twice as many green filters as it does either red or blue. The Bayer array (and any other arrangement of filters) introduces a "mosaic" pattern to the light intensity values captured in the photosite array 209, and so the "demosaicing process" step 207 is needed to create a final image 240 in order to get rid of the mosaic effect thus introduced.

The majority of the prior art inventions for grain quality sensing are based on the analysis of final, capture images 240. This limits these prior art inventions to accepting the "processing steps" (that is, steps 206, 207, and 208, as well as other processes built into modern digital cameras. Each of steps 206-208 may introduce changes in the creation of the final image 240 that ultimately must be "undone" during the grain quality determination process. In other words, prior art inventions which work by analyzing final captured images 240 are subject to the processing inherent in any modern digital camera or imaging device 220.

Figure 2B:
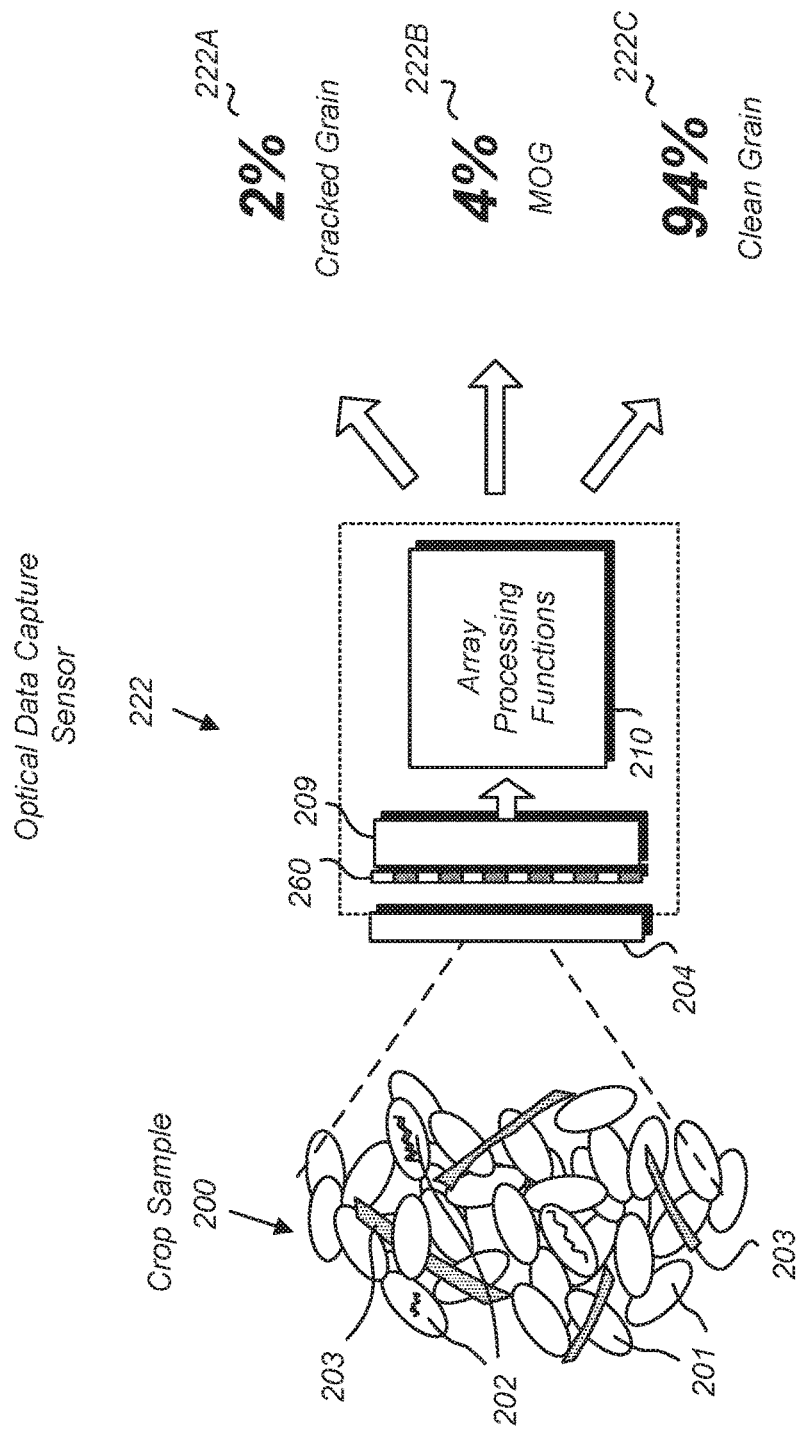
FIG. 2B shows a block diagram of an optical data capture sensor from the present invention and how it is used to determine the composition of a crop sample without taking images.

The present invention is an improvement in the art which "breaks open" the digital camera and looks at the raw photo data collected by the photosite array 209 without creating a captured image 240. Turning to FIG. 2B, an optical data capture sensor 222 comprises a lens 204 for capturing and directing photons of light into the photosite array 209. As with the imaging device 220 of the prior art, the photosite array 209 of the optical data capture sensor 222 is covered with a filter 260 for controlling which frequencies of photons (light) are taken in by the individual photosites in the photosite array 209.

The lens 204, filter 260, and photosite array 209 are the only components that the optical data capture sensor 222 has in common with the imaging device 220 of the prior art. The optical data capture sensor 222 does not do the same functions that are done by the analog electronics 205, analog-to-digital converter 206, demosaicing process 207, and digital imagine processing 208 of the prior art imaging device 220. The optical data capture sensor 222 also does not require a buffer 262 and image storage 264, as there is no final captured image 240 created.

In place of the functions described in the previous paragraph, the optical data capture sensor 222 uses the raw data collected by the photosite array directly, without processing it and converting it into a captured image 240. This is done in a series of array processing functions 210, which will be detailed in the discussion of FIGS. 3A-3C.

In an alternate embodiment of the present invention, the demosaicing process 207 may be added to the array processing functions 210 as a means of increasing the performance of the grain quality analysis. This will be explained in more detail in the discussion of FIGS. 3C and 3D.

The output of the array processing functions include information on the quality of the crop material 200, including the percentage of cracked grain detected (222A), the percentage of material other than grain, or MOG (222B), and the percentage of clean grain (222C). The information 222A, 222B, and 222C is calculated by the array processing functions 210 without ever creating a final captured image 240.

Figure 2C:
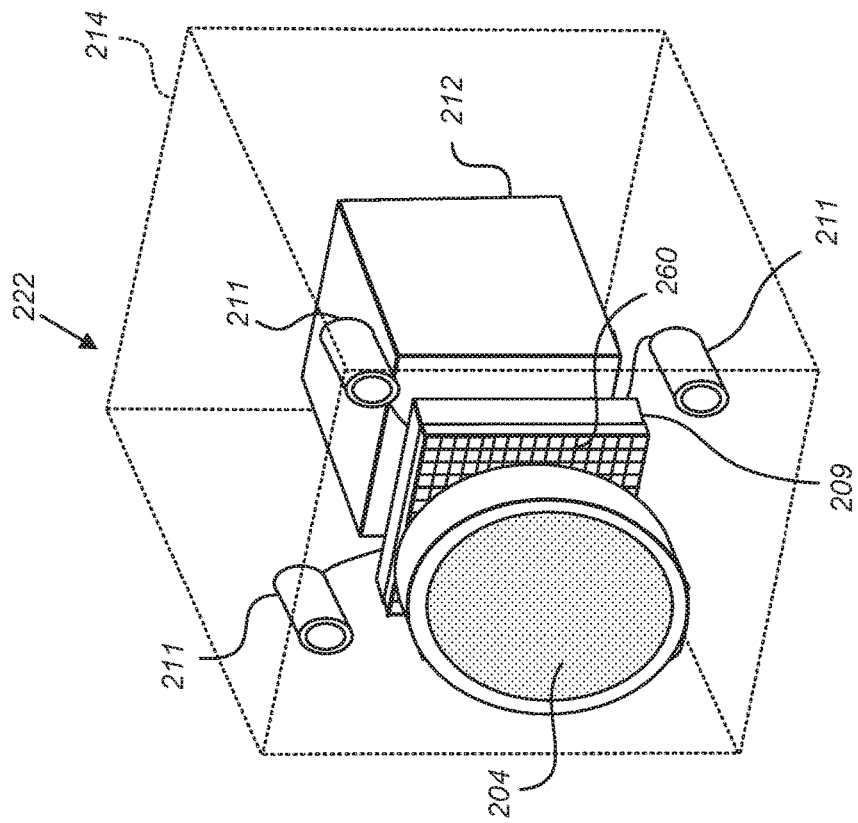
FIG. 2C is a perspective view of one embodiment of an optical data capture sensor form the present invention.
Figure 2C:
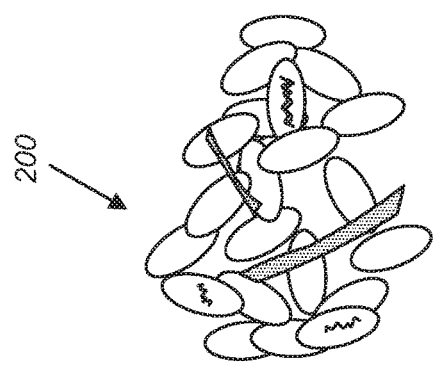

Moving to FIG. 2C, we see a perspective view of the optical data capture sensor 222. While FIG. 2B was intended to detail the functional aspects of one embodiment of an optical data capture sensor 222, FIG. 2C focuses more on the physical implementation.

FIG. 2C again shows the lens 204, the filter 260, and the photosite array 209, as before. In addition to these components, light sources 211 are added to FIG. 2C. These light sources 211 may be light emitting diodes (LEDs) or any other appropriate lighting source. The number of light sources 211 may vary from one embodiment to another, and the frequency of light emitted by each light source 211 may be of a different wavelength, as may be required to capture the appropriate photon data reflected back from the crop sample 200. The use of these light sources 211 in analyzing the crop sample 200 will be discussed shortly.

A processing unit 212 provides power for the photosite array 209 and light sources 211, controls the inputs and outputs from the optical data capture sensor 222, and performs the processing carried out by the array processing functions 210. The entire module may be enclosed in an outer enclosure 214, shown here as a dotted line.

Figure 2D:
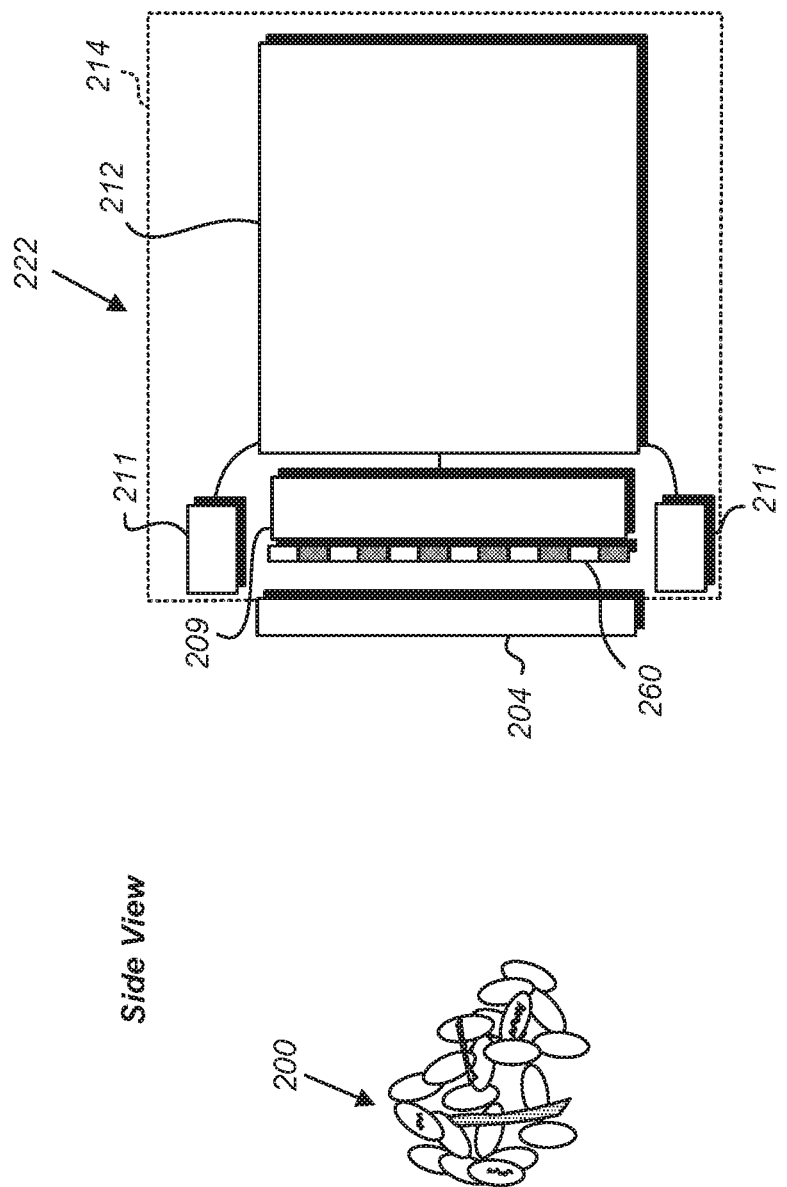
FIG. 2D is a side view of one embodiment of an optical data capture sensor form the present invention.

FIG. 2D is a side view of the embodiment of an optical data capture sensor 222 shown in FIG. 2C. It is provided to give an alternate view of the optical data capture sensor 222, but does not introduce any new functionality or components.

The following paragraphs shall describe one embodiment of an optical data capture sensor 222 and how it may be used to implement a grain quality sensor (also known as a "grain quality and cleanliness sensor"). The purpose of a grain quality sensor is to determine the levels of material other than grain (MOG) and broken kernels (cracked grain) in the clean grain path. The values are reported to the operator and provide inputs to the automation algorithm discussed later in this specification. The following description will refer to FIGS. 2B, 2C, and 2D and will use the reference designators collectively from these figures as needed.

In one embodiment of a grain quality sensor, the crop sample 200 is illuminated with light sources 211 which emit, at a minimum, ultraviolet light (UV), green light, and red light. The wavelengths of the green and red light sources 211 are used to provide the maximum contrast among the color photosites in the photosite array 209. In other words, the green light source 211 should produce minimal excitation in the red and blue photosites in the photosite array 209 (as dictated by the transmission curves of the color pattern filter 260).

Doing this will maximize the ability to perform coarse spectroscopy with the 3 different types of photosites in the array 209 (those receiving only green, those receiving only blue, and those receiving only red photons). The UV light source 211 is chosen to provide maximum contrast between the reflective starchy interior of the grain and the bran, or outer casing, while maintaining reasonable sensitivity of the photosite array 209 and transmission through the lens 204 and filter 260.

A processing unit 212 analyses the raw photosite array 209 data and determines the fractional amount of MOG and cracked grain so that it can be displayed to the operator and used as inputs to the automation algorithm.

Basic Algorithm: By shining light of different wavelengths on the crop sample 200, information can be gathered by the grain quality sensor (by the optical data capture sensor 222). Individual photosites from the array 209 which are dark (indicating relatively few photons of light collected in those areas) may indicate voids in the sample or noise and can be eliminated from consideration.

The inside of a grain kernel typically absorbs and reflects different wavelengths of light than the outer casing of the kernel. This fact can be used to detect damaged grain, as the wavelengths of light typically absorbed by the cracked, exposed inner kernel will be different than undamaged grain. The absorption and reflection of MOG will also be different than the absorption and reflection of clean grain and damaged grain.

The raw photosite array 209 data can then be analyzed for hue, saturation, and value (known as HSV by those skilled in the art, and also sometimes known as HSI, for hue, saturation, and intensity) to determine which photosites in the array 209 correspond to HSV values representing cracked grain, clean grain, and MOG. This algorithm is explained in detail in FIGS. 3A through 3D, and the corresponding discussion.

Variations on the Algorithm: Other color spaces can be used instead of HSV, for example, using the ab plane of the Lab colorspace. Lightness or value (intensity of the black and white image) may also be useful in identifying objects.

The image is broken into a series of sub-sections. Many of these sections will contain only grain and the spread in the corresponding distribution of values along any particular dimensions in whichever color space will be minimized. This minimum spread is used to determine the thresholds for the entire image.

Notes:

Hue is essentially the color of the light collected in the photosite array. Saturation or chroma is a measure of the purity of the color, so that white or gray are at one extreme and red, orange or another pure color are at the other extreme. Value is the lightness of the area, so that white and gray only vary in intensity.

Figure 2E:
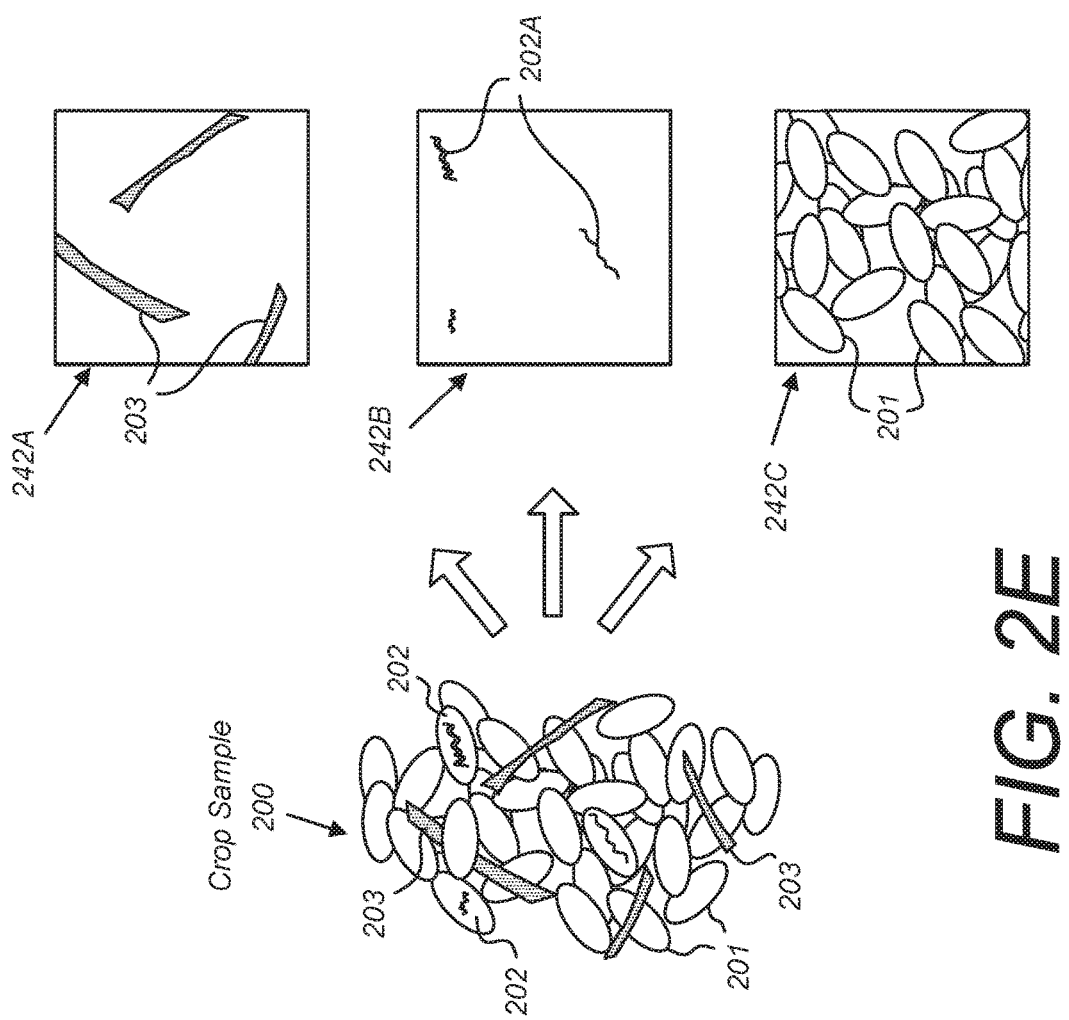
FIG. 2E illustrates how the present invention can create "partial images" or "layer images" that eliminate visual elements present in the original subject matter.

FIG. 2E illustrates how the present invention can create "partial images" or "layer images" that eliminate visual elements present in the original subject matter. It is important to note at this point that the creation of images as discussed here in FIG. 2E is not required for the optical data capture sensor 222 previously discussed. As stated then, the optical data capture sensor 222 does NOT use captured images 240 to determine information on the crop sample 200. This is a separate function which can be performed using the present invention.

The optical data capture sensor 222 can be used, as previously described, to detect which photosites in the array 209 contain information related to clean grain 201, damaged grain 202, and/or MOG 203.

It would be possible, therefore, to segment the photosites into one of these categories (clean grain, damaged grain, and MOG) and to then have an algorithm that will create "partial images" that do not faithfully reproduce the original subject matter (in this case, the crop sample 200), but instead show only subsets of the original sample 200. For example, one partial image 242A may show only the MOG 203 detected in a sample. Other partial images (242B and 242C) show only the damaged grain 202 (or just the damaged section of the grain kernels, 202A) or only the clean grain 201.

This "partial image" concept can be applied in areas other than grain quality sensing. For example, one can imagine a camera implementing this present invention (an alternate embodiment of the optical data capture sensor 222) which will eliminate certain color patterns from the final produced images, such as eliminating the blue sky from an outdoor picture, and possibly replacing it with another color, such as white or black.

Figure 2F:
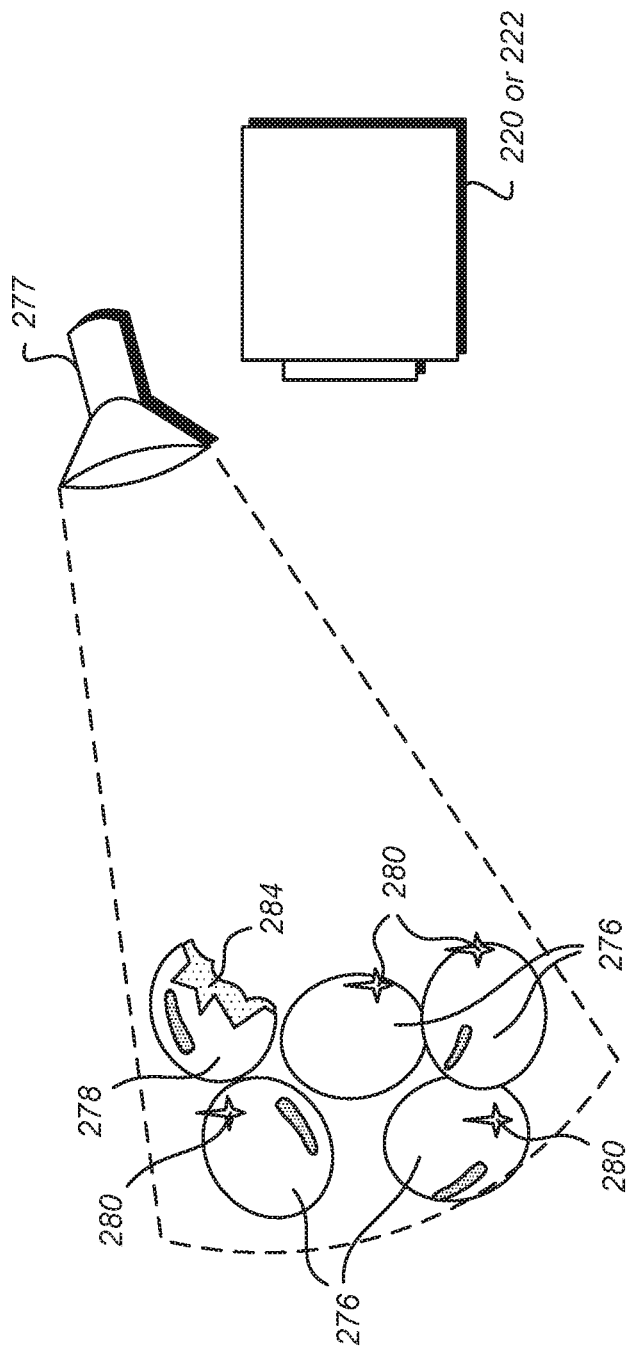
FIG. 2F illustrates an alternate embodiment of a grain quality sensor that detects damaged grain by detecting the lack of specular highlights on certain kernels.

FIG. 2F illustrates an alternate embodiment of a grain quality sensor that detects damaged grain by detecting the lack of specular highlights on certain kernels. The previous discussion of a grain quality sensor and/or an optical data capture sensor may not apply well for all types of seeds or kernels. For example, the inside of a soybean is essentially the same color as the outside casing of a soybean, so using the types of color-based analysis of the raw pixel data as previously described may not be effective. An alternate method of analysis may be required.

Turning to FIG. 2F, we see an assortment of whole soybeans 276 and broken soybeans 278. When a light source 277 is shown on the soybeans 276 and broken soybeans 278, we see that the outer casing of whole soybeans 276 is "shiny" and will produce specular highlights 280 which will appear as bright spots in an image taken of the crop. On the contrary, the inside surface 284 of a broken soybean 278 is not "shiny" and therefore does not produce a specular highlight 280. When an image is taken of the soybeans (276, 278) with an imaging device 220 or an optical data capture sensor 222, the image can be analyzed to look for the number of soybeans 276 with specular highlights 280 and the number or broken soybeans 278 without specular highlights 280.

It should be noted that, while the specification has previously discussed grain quality sensors that do not use images or image processing, standard image processing may be required to identify the specular highlights on soybeans or other similar crops.

Turning now to FIG. 2G, we see an image that has been processed to highlight "bright" spots or specular highlights. Each point in the image (or in the raw pixel data, if image processing is not used) is analyzed for brightness/intensity. Those falling below a certain threshold are shown as black or dark points on the resulting image, and those meeting or above the threshold will be shown as light or white points on the image. The result of this image processing will look like the image shown in FIG. 2G. Please note that white arrows are used in FIG. 2G in place of standard lead lines because of the dark nature of the image shown.

The processed image as shown in FIG. 2G will show whole soybeans as white or light colored outlines 288 each containing a bright spot representing a specular highlight 288A. Broken soybeans will show as white or light-colored outlines 286 without a specular highlight within the outline 286. Some broken soybeans may be shown as irregular shapes 286A, indicating they are not whole soybeans.

An algorithm looking for broken soybeans in an image processed in this manner could identify broken soybeans by looking for nonstandard shapes (such as 286A in FIG. 2G) or by looking for shapes that do not contain a bright spot 288A within the outline (such as 286 in FIG. 2G).

It is important to note that this alternate embodiment of a grain quality sensor that uses the presence of specular highlights to identify undamaged kernels or seeds will work with any crop type where the outside casing of the kernel or seed is reflective and the inside surface of the same type of kernel or seed is not. Soybeans are used in the example but are not intended to be limiting in any way.

It is also important to note that the approach discussed above might be used to help identify material other than grain, or non-crop material. In a crop such as soybeans, the expected outline of the kernels will be a certain shape (in this case, generally circular) and a certain size. Any outlines outside of those expected shapes and sizes (for instance, a rectangular shape for soybeans, or a size significantly larger than a typical soybean) are likely non-crop material. The presence of a specular highlight inside of one of these "outlier outlines" would help to identify the object as non-crop material, or to otherwise provide information on the nature of the object.

Figure 3A:
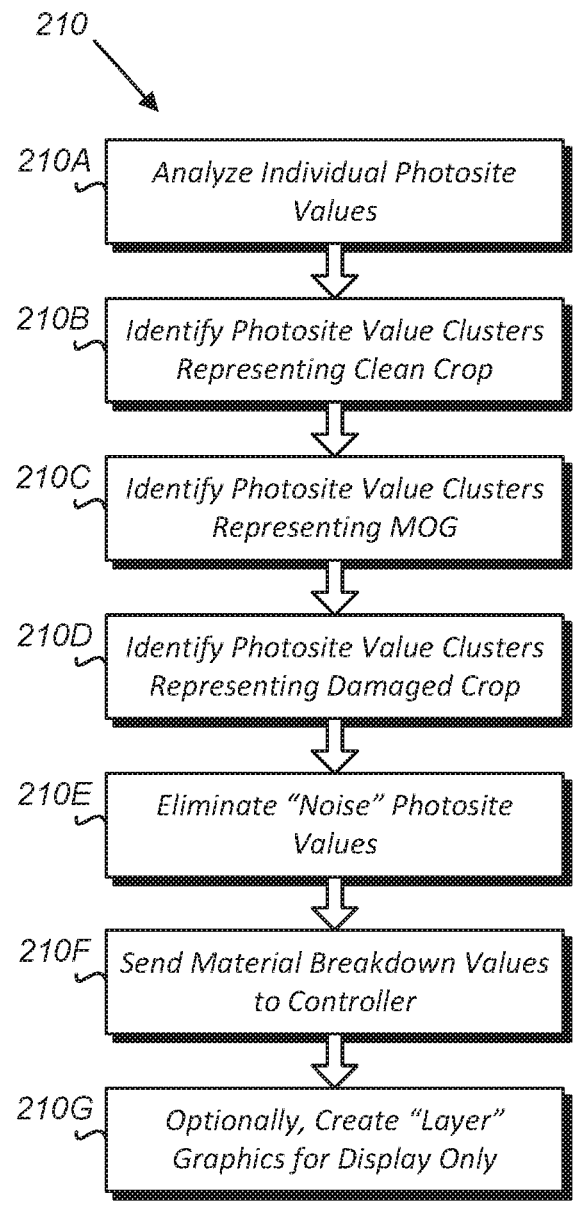
FIG. 3A is a flowchart showing the processes used to create the numeric values and other outputs of the optical data capture sensor of the present invention.

FIG. 3A is a flowchart showing the processes used to create the numeric values and other outputs of the optical data capture sensor of the present invention. The steps shown in FIG. 3A represent one embodiment only, and are not meant to be limiting, nor does the order of the steps shown in the flow necessarily mean that the steps shown have to be done in a certain order. The key concept captured in FIG. 3A is that all array processing functions 210 operate on individual photosite values (that is, on raw captured data) without producing a final image.

In Step 210A, each of the photosites in the photosite array 209 is analyzed to determine the number of photons detected (indicative of the amount of light received) and a determination is made as to the wavelength of light represented by each photosite based on the filter 260 that is covering the photosite array 209. In Step 210B, clusters of similar color levels are identified, and each cluster is compared to predicted values for clean grain to determine which of these clusters represent clean grain (or what percentage of the overall photosites in the array 209 appear to be representing clean grain). Steps 210C and 210D do the same analysis to determine the overall percentage of both MOG and damaged grain (or damaged crop), respectively. An optional Step 210E is performed in order to eliminate outliers or photosites that do not appear to match any of the surrounding photosite values (in other words, a single "dark" photosite surrounded by photosites representing clean grain is eliminated as probable noise.)

Finally, in Step 210F, the determined percentages (material breakdown values) determined in Steps 210B, 210C, and 210D are sent to the controller responsible for making automated adjustments to the combine or for displaying the values to an operator.

In optional Step 210G, "partial images" such as those discussed and shown in FIG. 2E may be generated for display to an operator.

Figure 3B:
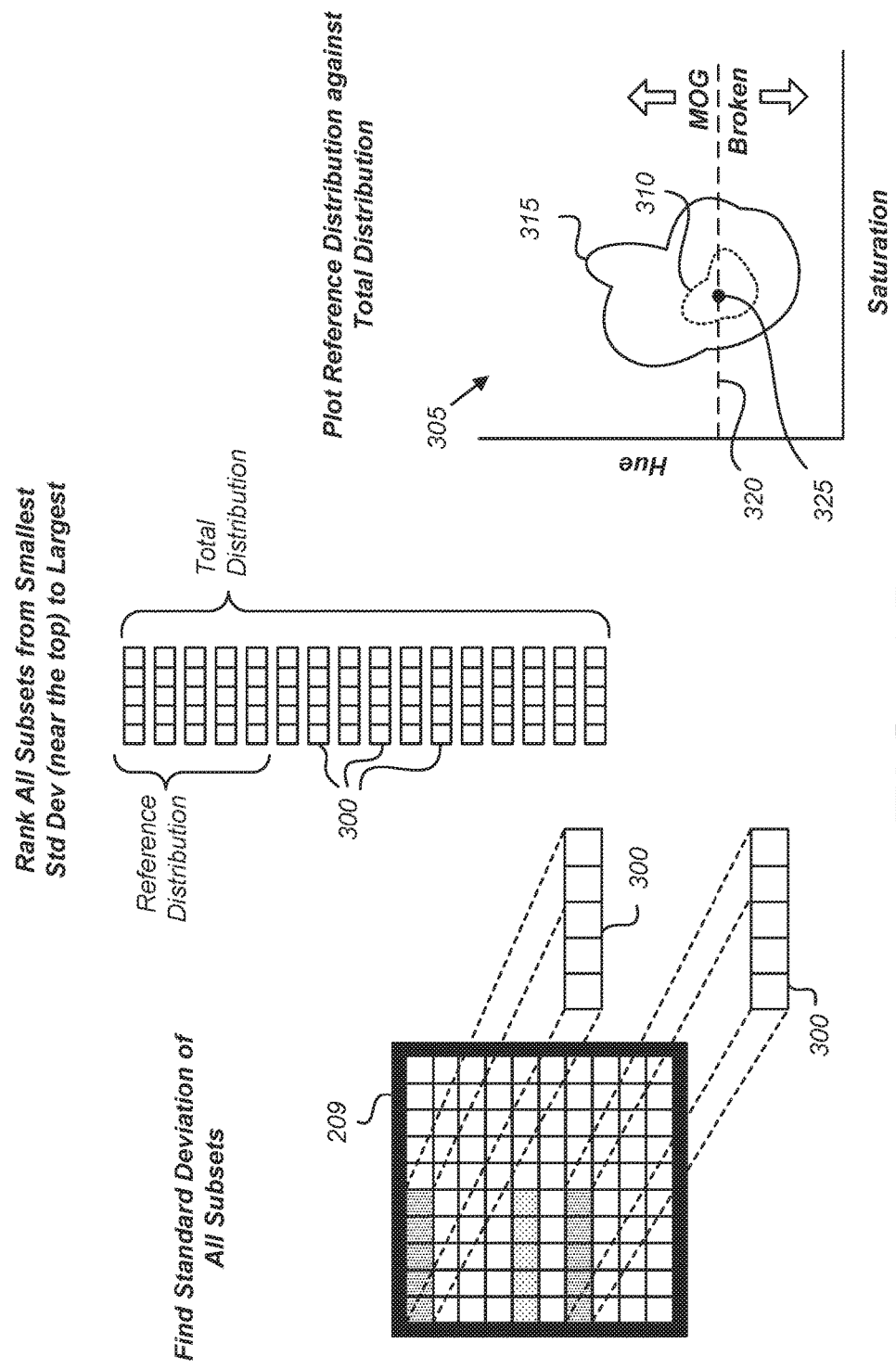
FIG. 3B illustrates one embodiment of an algorithm for analyzing values in a photosite array to determine the content of a grain or crop sample.

FIG. 3B illustrates one embodiment of an algorithm for analyzing values in a photosite array to determine the content of a grain or crop sample. Once raw data has been captured in the photosite array 209, all of the pixels in the array are grouped into subsets 300, and the "spread" of each pixel subset 300 is measured. In one embodiment, the "spread" is determined by taking the standard deviation of the pixels in the subset 300. If the standard deviation of a particular subset 300 is small, that means that all of the pixels in that subset 300 are close to the same color. A larger standard deviation in a subset 300 means that there is a larger "spread" or range of colors represented in the subset 300. In this example, which is meant purely for illustrative purposes, the size of the subset is 5 pixels, but any appropriate subset size may be chosen. Only a very small photosite array 209 is shown in FIG. 3B, just enough to illustrate the concept.

After the standard deviations for all of the subsets 300 have been determined, the subsets are placed in order by the size of the standard deviation. For example, in the center of FIG. 3B, the subsets 300 are shown arranged vertically from the smallest standard deviation at the top to the largest at the bottom. (This concept is shown graphically as a stack of subsets 300 in FIG. 3B, but the output in reality is a ranked list of standard deviations, from smallest to largest.)

Once the ranked list is created, a small number of subsets 300 near the top of the list (that is, the subsets 300 with the smallest standard deviations) are considered to be the "reference distribution," and the entire list of subsets 300 is considered to be the "total distribution."

The subsets 300 in the "reference distribution" should ideally be the subsets 300 that are closest to the desired color (for example, the color of clean grain). The histogram of the reference distribution can be plotted against the histogram of the total distribution of colors captured by the photosite array.

This is shown on the right side of FIG. 3B. In the plot of the histograms 305, the smaller dashed line represents the plot of the reference distribution 310. In this example, the histograms are plotted on a three-dimensional plot in the HSV color space (representing Hue, Saturation, and Value), but any other appropriate color space can be used with similar results.

It should be noted that the plot 305 is shown in only two dimensions (hue on the Y axis and saturation on the X axis), but there would also be a third axis rising up out of the figure, perpendicular to both the X and Y axes, and that would represent intensity. The intensity has been omitted for clarity in FIG. 3B, but its effect would be to give the histogram plots of the reference distribution 310 and the total distribution 315 a volume, with a third dimension of the two plots rising up out of the figure in the direction of the missing intensity axis.

The total distribution plot 315 is added to the histogram plot 305, superimposing it on the reference distribution plot 310. The total distribution plot 315 will always be at least as big as the reference distribution plot 310, but will typically be significantly larger, representing the larger color range present in the total distribution over the reference distribution. If the grain quality sensor is looking at a very pure sample of grain (that is, a sample that is almost 100 percent clean grain), the total distribution plot 315 may be almost as small as the reference distribution plot 310.

In one embodiment, the algorithm illustrated in FIG. 3B looks for the point of peak intensity 325 in the reference distribution plot 310. Although the intensity axis has been intentionally left off of the plot 305 shown here, the point of peak intensity 325 would be the point at which the reference distribution plot 310 extends the farthest into the intensity dimension (the tallest peak that would extend up out of the figure if intensity were plotted.

This point of peak intensity 325 is used to draw a separation line 320 on the graph perpendicular to the hue axis (it would be a plane if drawn in three dimensions). This line is used to determine relative percentages of clean grain, MOG, and cracked or broken grain in the following way:

A point inside the reference distribution plot 310 will be considered to represent clean grain.

A point outside of the reference distribution plot 310 and ABOVE the separation line 320 will be considered to represent MOG.

A point outside of the reference distribution plot 310 and BELOW the separation line 320 will be considered to represent cracked or broken grain.

The above bullets assume that the hues are plotted such that the colors representing MOG will be more likely found toward the top of the two-dimensional plot, and colors representing broken grain will be toward the bottom. The spectrum of hues could be plotted in reverse, and then the sides of the separation line 320 representing MOG and broken grain would be flipped.

In the method outlined above, the data captured in the photosite array 209 can be analyzed without ever forming an actual image. Stated another way, to create an image from the data captured by photosite array 209 the spatial information (that is, the location of each pixel in relation to every other pixel in the array 209, or its X-Y location in the array 209) must be maintained so that the data makes sense as an image. However, the algorithm described here and in FIG. 3B is only looking at the total distribution of colors in the photosite array 209, without caring about the locations in the photosite array 209 that held the data originally.

An analogy may help better illustrate this concept. Let's imagine that an "image" is the picture printed on a fully assembled jigsaw puzzle, and the unassembled pieces of the puzzle scattered over an area on a table represent the photons captured by the photosite array. In order for an "image-based" grain quality algorithm from the prior art to work, the "jigsaw puzzle" must first be completely assembled (representing the creation of an image) before those algorithms can work.

However, the algorithm illustrated in FIG. 3B does not care about the "image" on the assembled jigsaw puzzle; it only cares about the data represented by the individual puzzle pieces. The subsets 300 (from FIG. 3B) do not have to be created from pixels or elements from consecutive locations in the photosite array 209. The algorithm of the present invention would work if someone randomly picked puzzle pieces from the box (representing random elements in the photosite array) to form each subset, and the actual puzzle never has to be assembled (that is, no image ever has to be created).

Figure 3C:
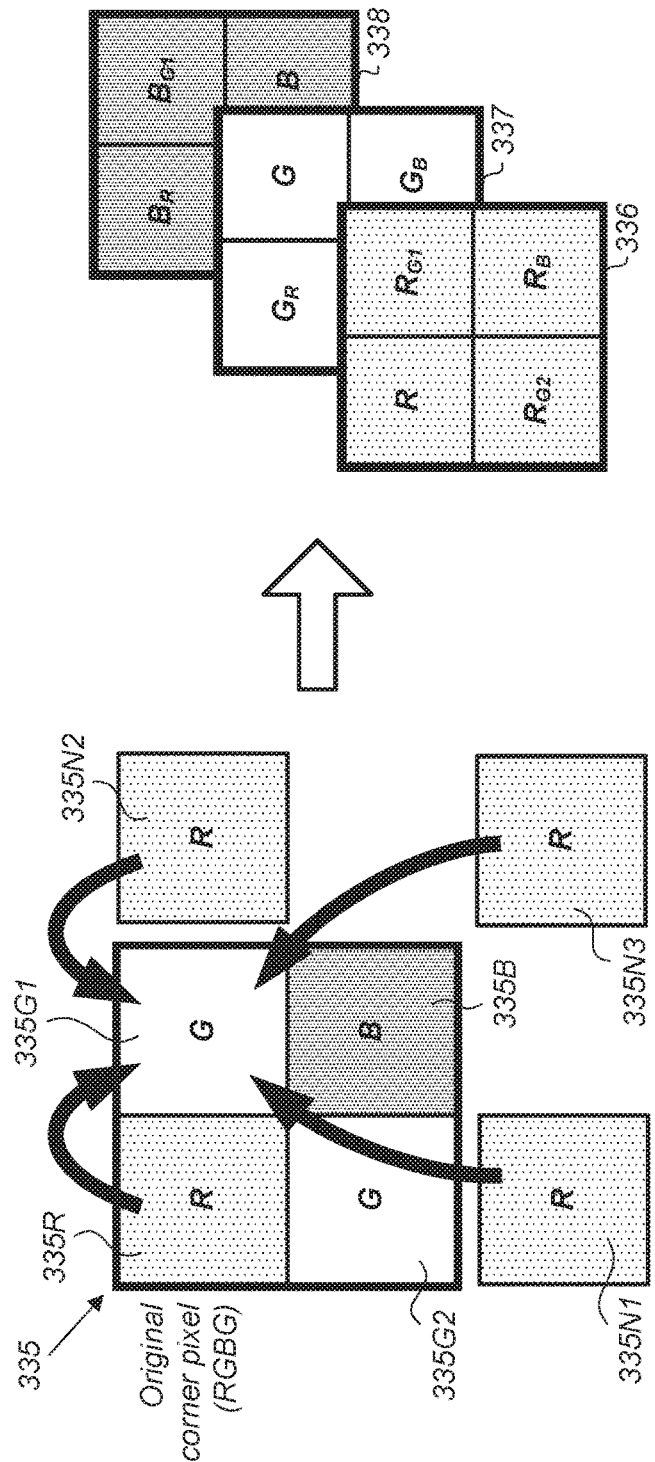
FIG. 3C describes how the demosaicing process of the prior art works.
Figure 3D:
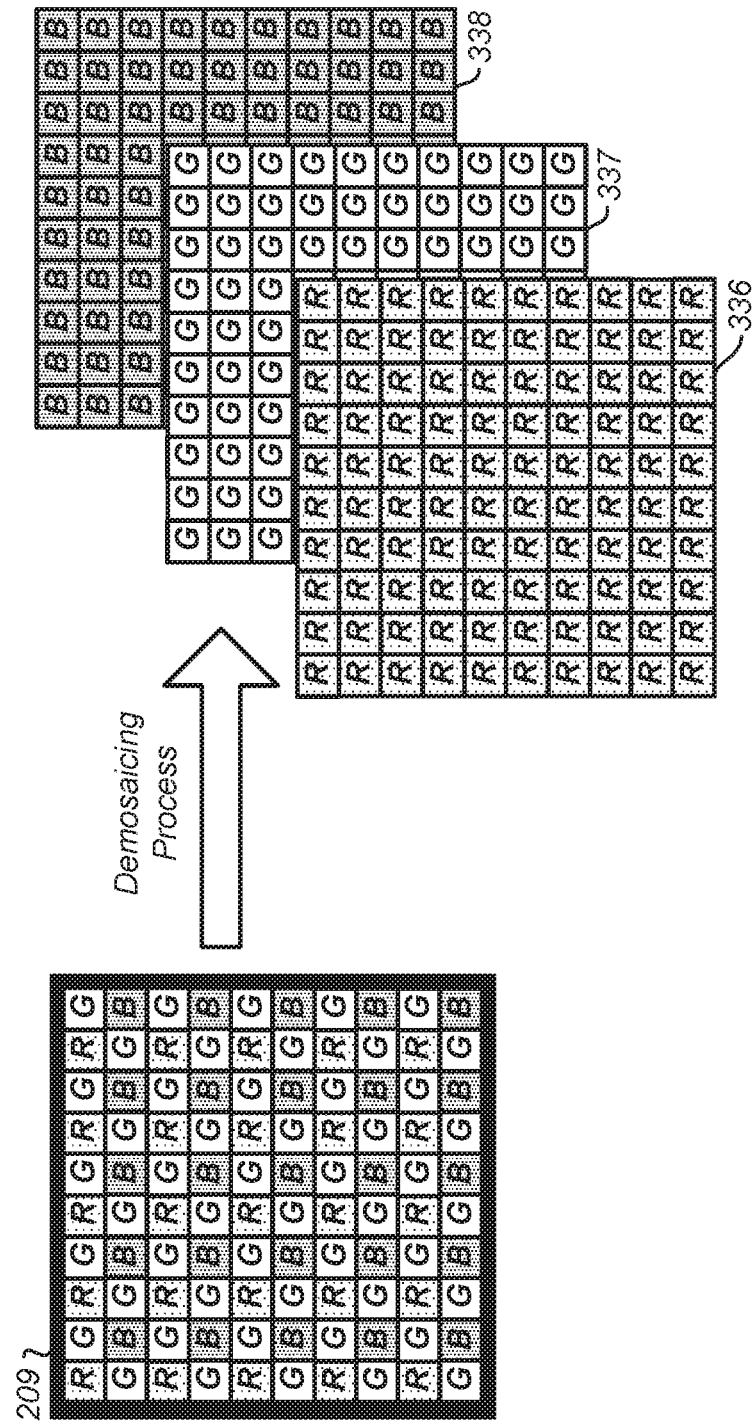
FIG. 3D illustrates how introducing the demosaicing process of the prior art into the process of FIG. 3A may improve performance.

Even though the demosaicing process previously discussed in this specification does not have to be used in the algorithm of the present invention, since no image needs to be created, it can be applied to the data in the photosite array 209 to achieve improved results, as is described briefly in FIGS. 3C and 3D.

FIG. 3C describes how the demosaicing process of the prior art works in very high-level terms. It has been discussed previously in this specification that a color filter is placed on top of the photosite array 209 so that each individual "bucket" or element in the photosite array 209 will only capture one color of photon (either red, green, or blue). Turning to FIG. 3C, we focus on a single pixel 335 taken from the upper left corner of the photosite array 209 to describe the process. Each pixel 335 on a photosite array 209 is represented by four elements in the photosite array 209, one red-filtered element 335R, two green-filtered elements 335G1 and 335G2, and one blue-filtered element 335B. For discussion purposes, we will focus on the 335G1 element in FIG. 3C. When the photosite array 209 is used to capture raw photons, it is very likely that photons of red, green, and blue light will all strike the 335G1 element, but, because of the green filter over 335G1, only the green photons will be allowed to actually enter the 335G1 element. Because of this filtering, the 335G1 element will likely be missing detail that is in the point in the physical world corresponding to element 335G1 (that is, the blue and red photons that may have hit the element but been rejected and not counted).

The demosaicing process from the prior art can be used to correct this deficiency. In order to determine the amount of red photons that may have hit the 335G1 element and been rejected, an algorithm can look at the closest red-filtered elements and estimate the amount of red that may have hit 335G1 based on the number of red photons the closest red-filtered elements received.

For example, for element 335G1, an algorithm may look at the red-filtered elements 335R, 335N1, 335N2, and 335N3 to see how many red photons they captured. The red-filtered elements closest to 335G1 (such as 335R and 335N2) will have a greater effect on the calculated red value for 335G1 than those red-filtered elements farther away (such as 335N1 and 335N3). By looking at the closest red-filtered neighbors, an estimated value for the number of red photons that were likely received at element 335G1 is calculated. This new value is put into a new "red-value array" 336 as value $R_{G1}$, in the location corresponding to the 335G1 element in the original photosite array 209.

Using this method, the demosaicing process will create a new red-value array 336 the same size as the original photosite array 209, as well as a green-value array 337, and a blue-value array 338. The result of this process is that there is now three times as much information (represented by the three arrays 336, 337, and 338) than was captured in the original photosite array. This increase in data can improve the results achieved by the grain quality sensor of the present invention.

FIG. 3D does not introduce any new concepts, but shows the results of the process from a higher level of abstraction, showing that the data captured originally in the photosite array 209 is multiplied in the process, outputting arrays 336, 337, and 338, one array corresponding to each of the three colors.

Figure 4A:
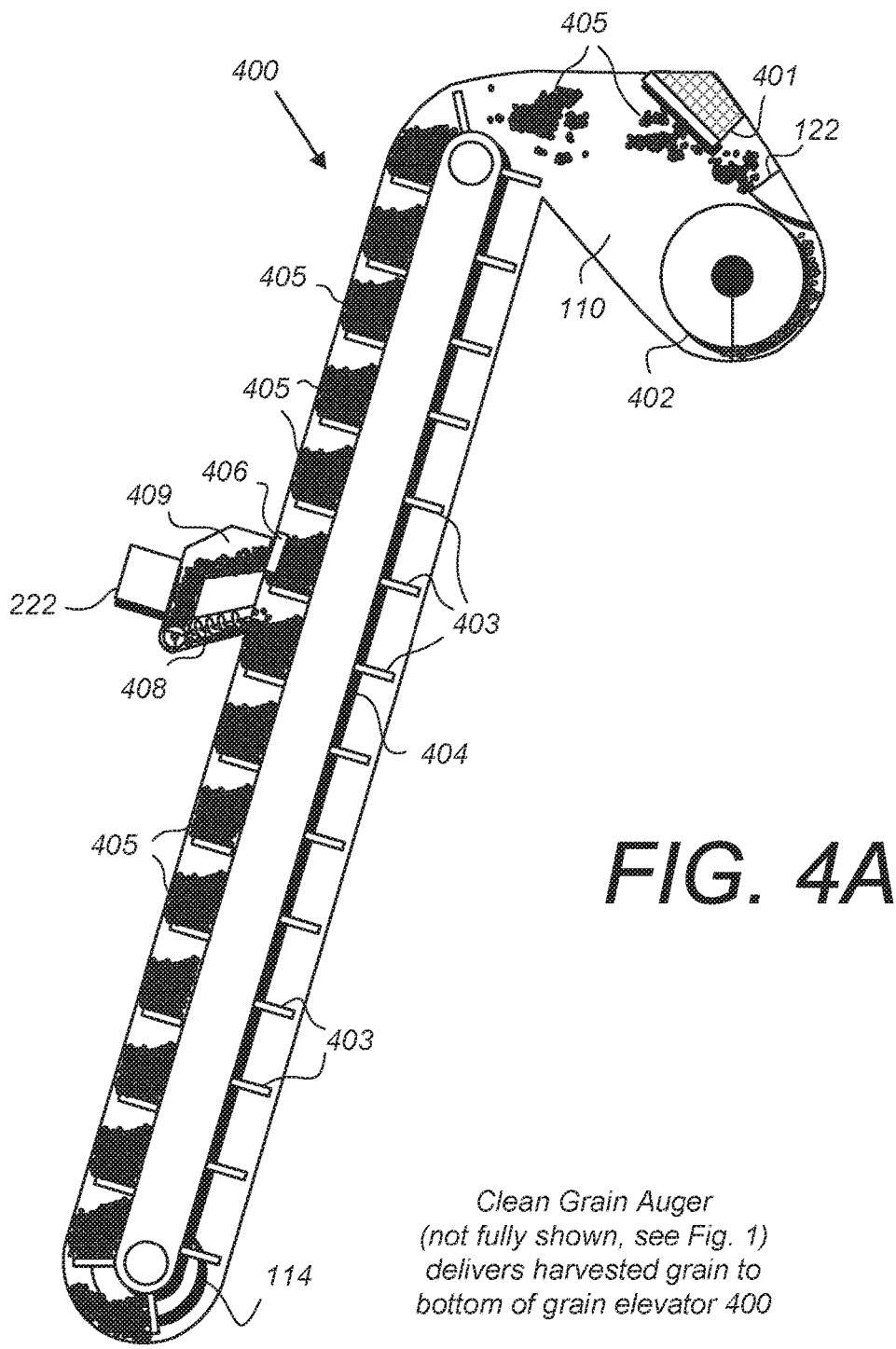
FIG. 4A shows the clean grain elevator of a typical combine and the sensors associated with the clean grain elevator as defined for use in the present invention.

FIG. 4A shows the clean grain elevator of a typical combine and the sensors associated with the clean grain elevator 400 as defined for use in the present invention. The clean grain elevator 400 in a combine provides a mechanism for delivering the collected (harvested) grain from the clean grain auger (114, FIG. 1) to the clean grain tank 110. Note that the clean grain auger 114 is partially obscured in FIG. 4A (as it would be behind the bottom of the clean grain elevator 400), but it delivers the "clean grain" collected at the bottom of the cleaning shoe 117 to the clean grain tank 110. Refer to FIG. 1 and FIG. 4A to identify all of the parts referenced herein.

Returning to FIG. 4A, we see that clean grain (or simply "grain") 405 is delivered into the bottom of the clean grain elevator 400 by the clean grain auger 114. Paddles 403 mounted on a delivery conveyor 404 rotate up through the clean grain elevator 400 to deliver the grain 405 to the clean grain tank 110. (Note: In the example shown in FIG. 4A, the conveyor 404 and paddles 403 rotate in a clockwise manner.)

The optical data capture sensor 222 will be mounted such that it can examine the grain 405 before it is deposited in the grain tank 110. There are several methods of mounting the optical data capture sensor 222 to the clean grain elevator 400, and one possible embodiment of such a mounting method is shown in FIG. 4A. In this mounting method, an opening 406 is made in the side of the clean grain elevator 400 such that some of the grain 405 spills into a viewing chamber 409 which is mounted on the clean grain elevator 400. The grain 405 travels through the viewing chamber 409 and is "presented" to the optical data capture sensor 222. The optical data capture sensor 222 is mounted to the viewing chamber 409 such that the lens 204 of the optical data capture sensor (see FIG. 2B) is focused on the contents of the viewing chamber 409. The optical data capture sensor 222 is activated to illuminate the grain 405 held in the viewing chamber 409 and capture photons reflected from the grain 405 using the photosite array (209, see FIG. 2C). Once the data is collected form the grain 405, a return auger 408 takes the sampled grain 405 and deposits it back into the clean grain elevator 400 so that it can continue its journey into the clean grain tank 110.

It should be noted that this method of mounting the optical data capture sensor 222 to the clean grain elevator 400 is only one embodiment, and other means of mounting the optical data capture sensor 222 to the clean grain elevator 400 do exist and may be used in place of the method shown in FIG. 4.

Figure 4B:
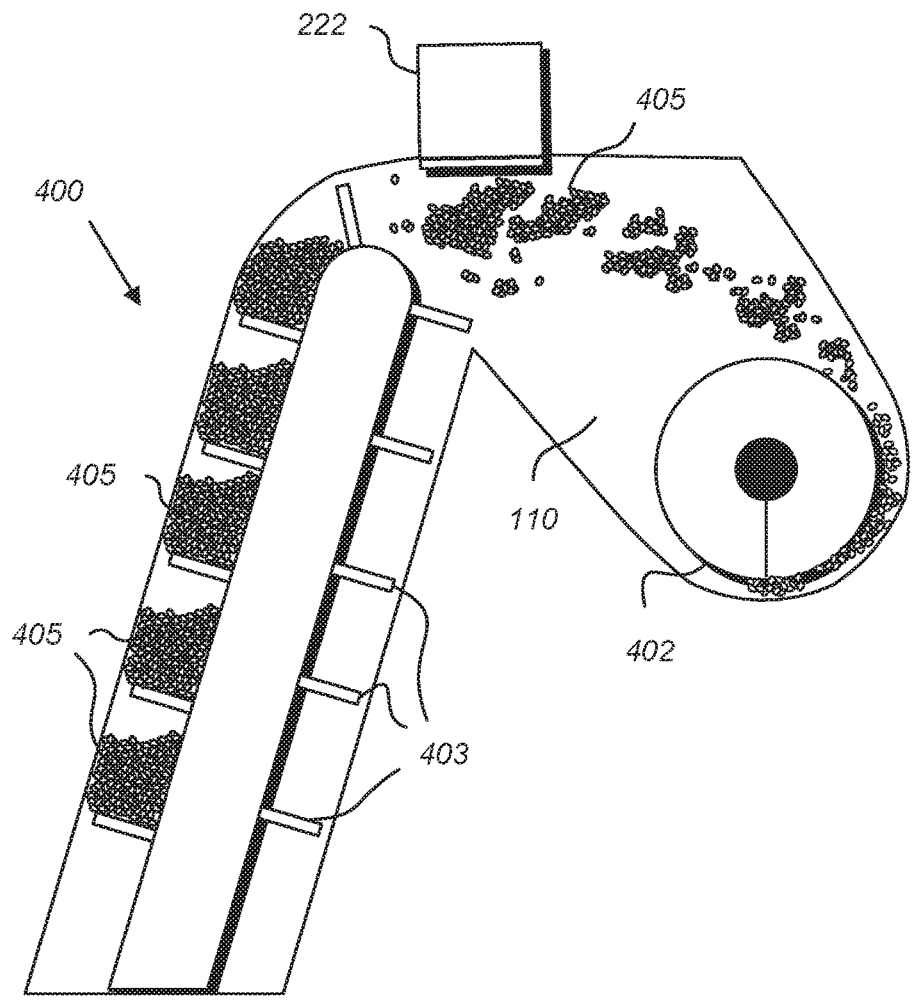
FIG. 4B shows an alternate mounting location and system for the optical data capture sensor (grain quality sensor) of the present invention.

FIG. 4B shows an alternate mounting location and system for the optical data capture sensor 222 (such as a grain quality sensor) of the present invention. The upper portion of a clean grain elevator 400 is shown, showing the paddles 403, grain 405, clean grain tank 110, and unloading auger 402. The yield sensor 401 and moisture sensor 122 shown in FIG. 4A have been removed in FIG. 4B for clarity. In this alternate mounting scheme, the optical data capture sensor 222 is mounted at the top of the clean grain elevator 400, right above the point where the grain 405 is thrown off of the paddles 403 into the clean grain tank 110.

In this location, the optical data capture sensor 222 does not need to have the viewing chamber 409 or the return auger 408, as the flow of grain 405 is not interrupted (no sampling from the elevator 400) is required. Instead, in this location, the optical data capture sensor 222 will capture raw photon data as the grain 405 flies past the optical data capture sensor 220. By capturing photon data as the grain 405 is in flight, a better representation of the grain 405 may be obtained, as it is not packed into a tight viewing chamber 409.

IV. Yield Sensor and Moisture Sensor

Returning now to look at FIG. 4A, at the top point of the conveyor 404, the grain 405 is thrown into the tank 110 by centrifugal force as the paddles 403 switch directions and begin the descent back down the clean grain elevator 400. Inside the clean grain tank 110, there are optionally two additional sensors provided to collect data for use on the combine.

A yield sensor 401 is placed in the path of the grain 405 that is ejected from the paddles 403. Grain 405 strikes the yield sensor 401 and the yield sensor 401 calculates the amount of grain 405 striking it and calculates the approximate yield (amount of clean grain) entering the tank at any given moment.

The yield sensor 401 may be implemented by a variety of methods. One common method in used today is to have the grain 405 hit an impact plate attached to a load sensor. The force of the grain 405 hitting the impact plate allows the approximate load to be measured and allowing a derivation of approximate mass or material flow rate.

Another means of creating a yield sensor is to base the sensor on an acoustic chamber such as that used by the energy sensing acoustic technology (ESAT) sensors manufactured by Appareo systems, including those disclosed in WO/2012/125575, the publication of which is incorporated herein by reference in its entirety, including the system and method for determining yield and/or loss from a harvesting machine using acoustic sensors, as disclosed in US/2014/0135082, the publication of which is incorporated herein by reference in its entirety, or variants thereof of any of the above described acoustic sensor technologies. An acoustic sensor such as those described in the referenced documents determines the amount of the yield based on the amount of sound generated by an impact on an impact plate sitting atop an acoustic chamber.

Yet another alternate method of determining the yield would be to place load sensors on the upper bearings of the conveyor 404 in the clean grain elevator 400. The load on the sensors could be taken when the clean grain elevator 400 is empty, and then compared to the load on the conveyor 404 when material is flowing through the clean grain elevator 400. The load value when the clean grain elevator 400 is empty could be measured once during a configuration step (perhaps as part of a factory configuration step) and stored in non-volatile memory for subsequent comparison to the load value when crop is present. The difference between the two readings would represent the mass of the clean grain (and hence give the yield).

Any other appropriate method of determining yield may be used without deviating from the intent of the present invention.

In addition to a yield sensor, a moisture sensor 122 may also be placed inside the clean grain tank 110. There are various ways to implement a moisture sensor 122 available in the art. One such common type of moisture sensor 122 is a capacitive sensor. A capacitive sensor measures moisture by monitoring the change in the dielectric properties of grain. Another common type of moisture sensor 122 uses near-infrared (NIR) wavelengths of light to detect moisture. This is done by shining two different wavelengths of NIR on a sample. One of the wavelengths is calibrated for moisture and the other as a reference. The ratio of the two signals is derived electronically to calculate the moisture content. The convoluted nature of NIR spectra can require broadband illumination, a spectrometer, and chemo-metric calibration methods to accurately extract moisture. Often the moisture sensor 122 collects samples of crop 405 in the clean grain tank 110 in a funnel-shaped cup, performs the analysis, and then releases the crop 405 such that it drops to the bottom of the tank 110 and can be offloaded subsequently by an unloading auger 402.

One improvement on the prior art use of NIR moisture measurement is the used of two or more MEMS spectrometers. MEMS spectrometers are smaller and less expensive than traditional spectrometers, making them perfectly suited for such applications. When at least two spectrometers are used, one could be used to measure the crop sample and the other could be used to measure the light source itself. The spectroscopic measurement of the light source can be used as the "standard" or control data against which the spectroscopic measurement of the crop sample is compared, allowing for highly accurate measurements that are free from environmental variations.

FIG. 4A illustrates one embodiment of an optical data capture sensor 222, a yield sensor 401, and a moisture sensor 122. The example illustration in FIG. 4A is not intended to be limiting, and other embodiments of the sensors can be created without deviating from the inventive concept captured herein. These sensors provide data items which may be used independently (perhaps displayed to an operator), or in some combination in a combine control algorithm.

V. Look-Ahead and Look-Aside Crop Mass Sensor

Figure 5:
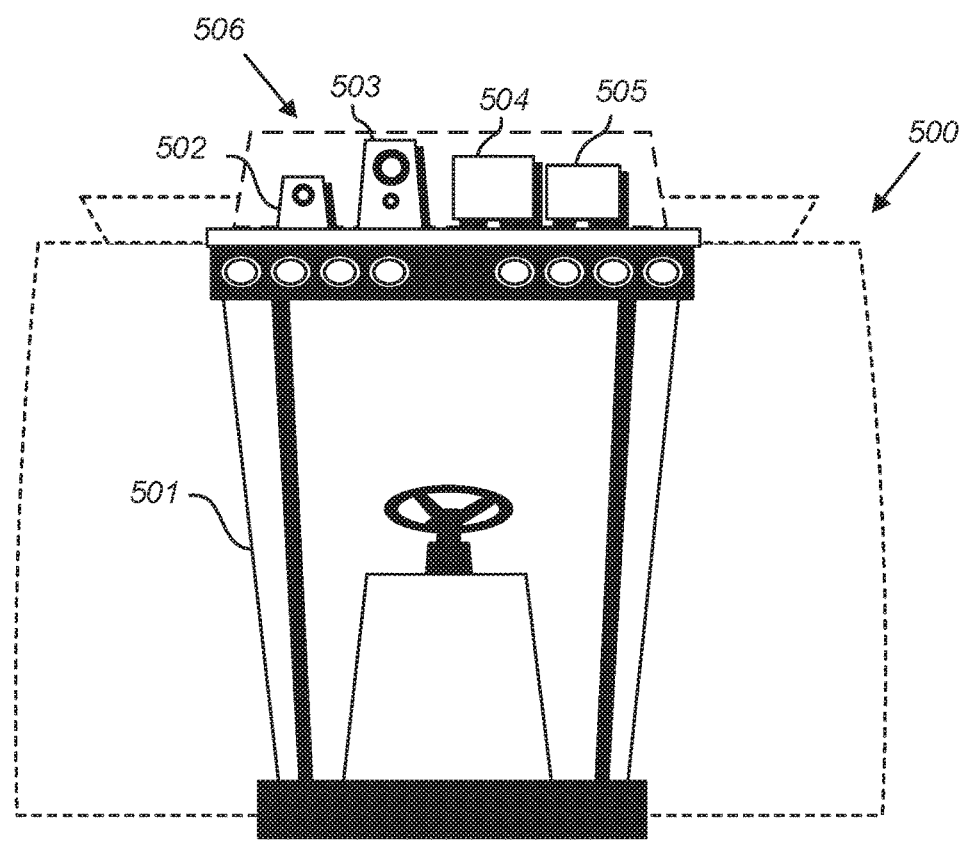
FIG. 5 shows the main functional components of one embodiment of a look-ahead sensor of the present invention.

FIGS. 5 through 6J detail one or more embodiments and components of a mass load detection sensor (also called a "crop mass sensor") which can be used to predict the amount of crop material that is about to enter the combine at any given moment in time. There are two main embodiments of a crop mass sensor discussed herein: a "look-ahead" crop mass sensor which senses mass immediately in front of the combine, just before it enters the combine, and a "look-aside" crop mass sensor, which functions essentially identically to the look-ahead sensor but focuses sensors to the side of the combine instead of just in front of it, where the improved viewing angles for sensors (the ability to look straight down on the crop from above, versus trying to detect mass by looking out ahead of the vehicle) can give improved performance. Sensing mass to the side of the combine instead of directly in front of the combine also means that the mass data being calculated will have to be stored and used on the subsequent pass of the vehicle (instead of being used almost immediately with the look-ahead embodiment). Unless otherwise specified, the functional description below will apply to both the "look-head" sensor and the "look-aside" sensor, even if only one type of the two sensors is discussed.

FIG. 5 shows the main functional components of one embodiment of a look-ahead sensor of the present invention. A subset of the components shown here may be used to detect crop mass.

Several sensing technologies may be used separately or in combination to detect crop mass. These technologies are shown in FIG. 5. The sensors described will be mounted to a combine 500 and in one embodiment may be mounted to the top of the combine cab 501, as shown in FIG. 5, although other mounting locations are possible.

A look-ahead sensor 506 is shown in FIG. 5 as a collection of sensors in a common housing, shown as a dashed line. Other embodiments of the look-ahead sensor 506 may exist which do not have a common housing, and which may have only a subset of the sensor technologies shown here.

In the embodiment of the look-ahead sensor 506 shown here, the look-ahead sensor 506 comprises a imaging device 502, a LIDAR sensor 503, and two radar sensors, one radar at a frequency that is absorbed by water 504 and one radar at a frequency that will pass through the crop to detect the ground beyond or beneath the crop 505. Each of these components shall be described separately in the following paragraphs.

VI. Imaging Device 502

A visible-spectrum, high-resolution camera or imaging device 502 will record video footage of the combine harvesting the crop. Imagine processing algorithms will be used to analyze the captured images and video to help provide data that can be used to determine crop mass.

The type of image processing algorithm used may be dependent on the type of crop being analyzed. For example, a flood fill algorithm could be used for wheat to look for areas of similar texture and/or color. More advanced algorithms can be used to more accurately determine crop density. One possible implementation of the imaging device 502 that is commercially available is a Basler Ace acA19t20-25gc camera with a 6 mm lens, although any appropriate imaging device could be used.

VII. LIDAR Sensor 503

A LIDAR system or LIDAR sensor 503 will also be used to help determine crop mass in some embodiments of the crop mass sensor 506. A 2D/3D LIDAR 503 works by firing pulses of laser light at a target and determining the distance to the target by measuring the time it takes for the light from the laser to be reflected back to the LIDAR 503 sensor.

By moving the LIDAR 503 forward (that is, by moving the combine 500 forward, thereby effectively moving the LIDAR 503 forward deeper into the crop) and constantly taking measurements, a three-dimensional model of the can be constructed layer by layer as the LIDAR 503 takes new readings on the distance of the continually changing front edge of the crop.

When using a LIDAR system 503 during harvesting, some of the laser pulses will not hit the crop, passing through to the ground. The remaining pulses will hit the crop and reflect back. The ratio of pulses that hit the ground to pulses that hit the crop helps to determine crop thickness. One possible embodiment of the LIDAR sensor 503 that is commercially available is a Hokuyo UTM-30LX-EW, although any appropriate LIDAR sensor or similar technology could be used.

VIII. Radar

The radar system will use two distinct radar bands. The frequency band of the moisture-detecting radar 504 will be such that it is strongly absorbed by moisture (and therefore crop material which has a measurable water content), and the non-moisture detecting radar 505 will be weakly absorbed by water and thus will pass through to the ground. The ratio between or distance between absorbed energy (from radar 504) and reflected energy (from radar 506) will be used to help correlate the crop density.

An example product that might be used for the moisture-detecting radar 504 is Delphi RSDS 77 GHz radar, although any appropriate type of radar capable of being absorbed by moisture could be used.

An example product that might be used for the non-moisture-detecting radar 505 is a 24 GHz radar system from Delta Mobile, although any appropriate type of radar capable of being passed through moisture could be used.

FIG. 6A shows a top view of a combine showing how the radar-based components of the look-ahead sensor of FIG. 5 would work to help predict incoming crop load. The look-ahead sensor 506 will emit two separate frequencies of radar energy, one that is strongly absorbed by moisture 601 and one that will pass through the crop 602. The differences between the moisture-absorbing band 601 and the non-moisture-absorbing band 602 can be used to help calculate the amount of crop matter 610 is present in proximity to the combine 500, and which is about to enter the combine header 523 to be cut and pulled into the machine. The arrow 651 indicates the forward direction of travel for the combine 500.

Figure 6B:
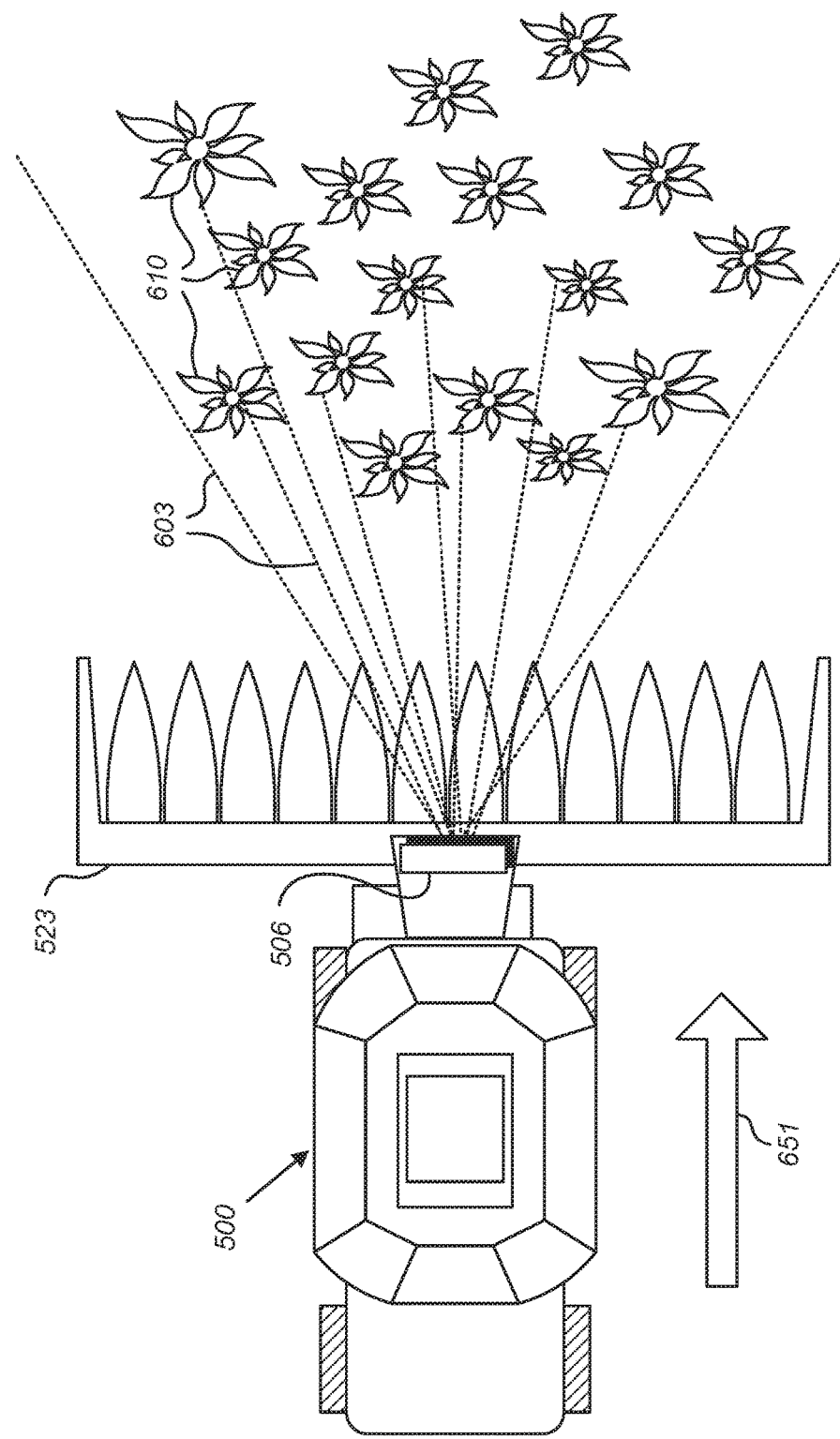
FIG. 6B shows a top view of a combine showing how the LIDAR-based component of the look-ahead sensor of FIG. 5 would work to predict incoming crop load.
Figure 7A:
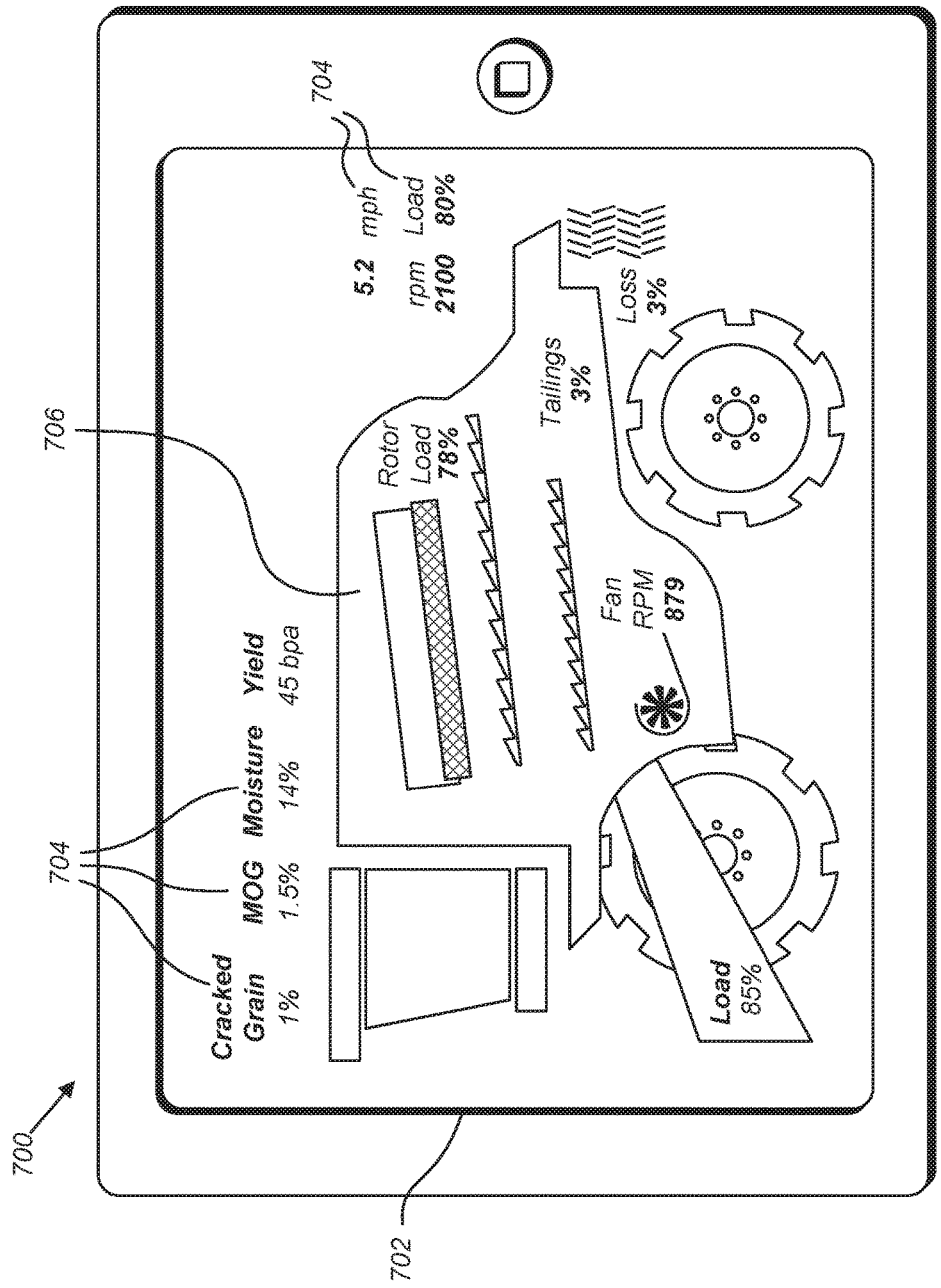
FIG. 7A shows one embodiment of an application user interface page for the present invention as displayed on a mobile computing device.
Figure 7B:
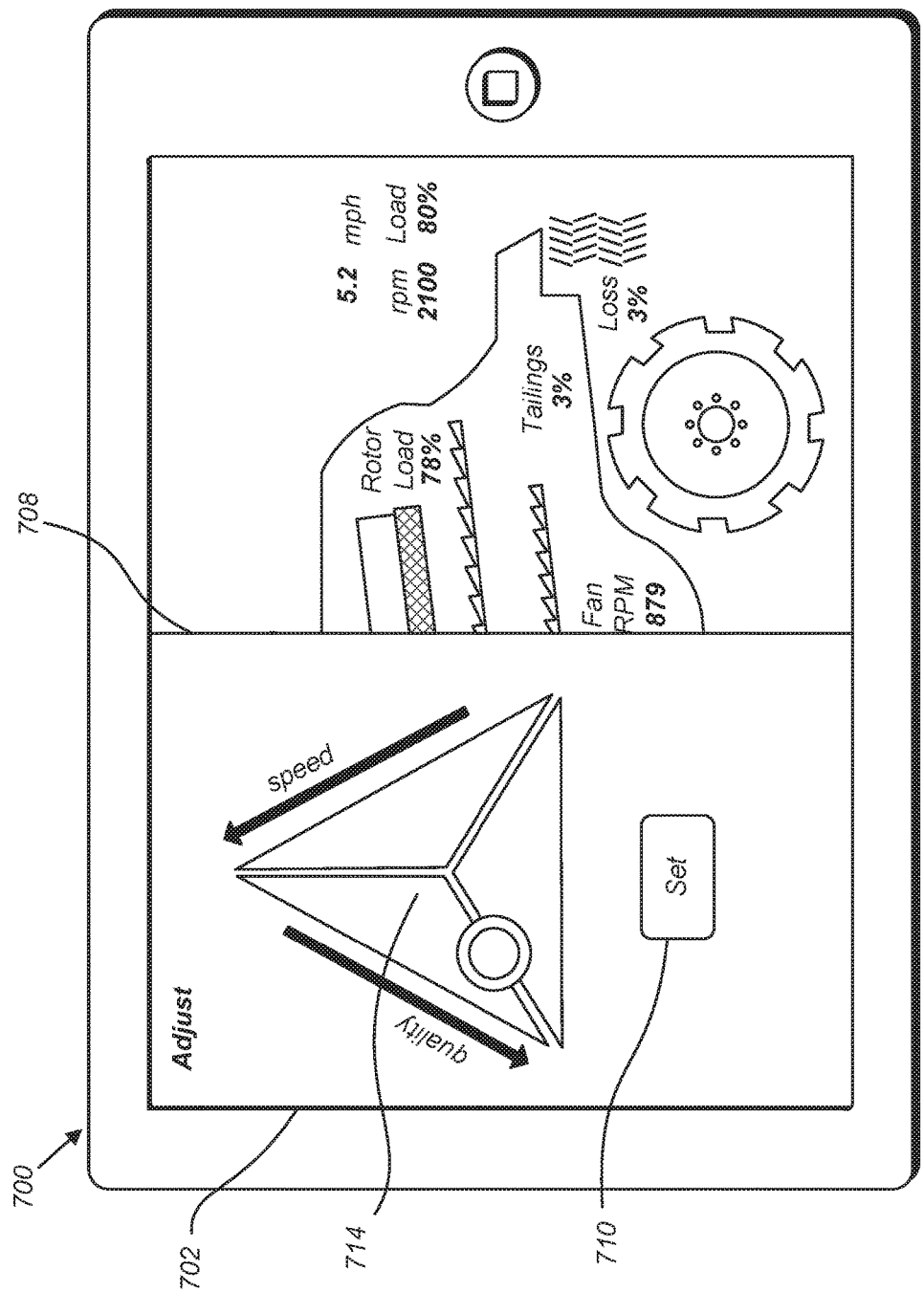
FIG. 7B shows another embodiment of an application user interface page for the present invention as displayed on a mobile computing device.

FIG. 6B shows a top view of a combine showing how the LIDAR-based component of the look-ahead sensor of FIG. 5 would work to predict incoming crop load. The look-ahead sensor 506 will emit beams of focused light 603 that will either strike crop matter 610 and be reflected back or will miss the crop matter 610 and not be reflected back, or have a reflection that is significantly delayed and or reduced by bouncing off the ground instead of the closer crop material. The differences between the light sensed reflecting back from the crop matter and that not being reflected back can be used to help calculate the amount of crop matter 610 is present in proximity to the combine 500, and which is about to enter the combine header 523 to be cut and pulled into the machine. The arrow 651 indicates the forward direction of travel for the combine 500.

Figure 6C:
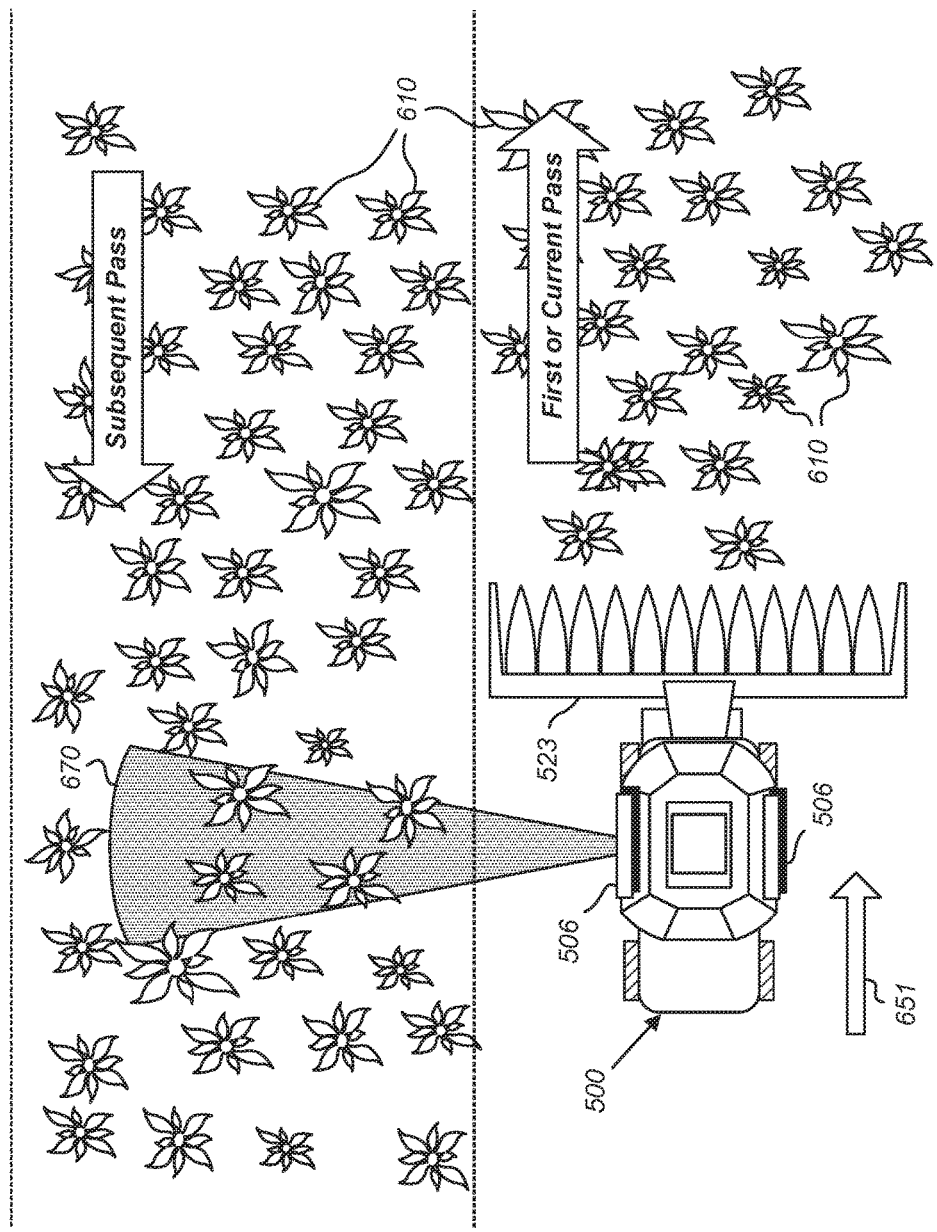
FIG. 6C shows a top view of a combine using an alternate embodiment of the look-ahead sensor of the present invention which looks to the side of the combine, instead of ahead of the combine.

FIG. 6C shows a top view of a combine using an alternate embodiment of the look-ahead sensor of the present invention which looks to the side of the combine, instead of ahead of the combine. In this embodiment of the crop mass sensor 506, the crop mass sensor 506 is focused to the side of the combine 500 instead of to the front of the combine 500. In FIG. 6C, the broadcast energy 670 is meant to represent all of the different sensing technologies that may be present in the crop mass sensor 506, including, in some embodiments, the video sensing, LIDAR light energy, and radar frequencies previously discussed in this specification, or some subset thereof (or potentially with additional technologies not discussed herein).

By focusing the "look-aside" sensor (functionally equivalent to the look-ahead sensor or, more generically, the crop mass sensor, and thus shown using the same reference number 506) to the side of the combine 500 instead of in front of the combine 500, the look-aside sensor 506 has an improved angle for sensing crop mass, as the broadcast energy 670 can be projected down on the crop material 610 at a steeper, more vertical angle, allowing better detection of crop material 610 versus trying to look out ahead of the combine 500.

This may require that two look-aside sensors 506 be mounted on the combine 500, such that the mass can be detected on either side of the combine 500 depending on the direction the combine 500 is traveling. Alternately, one look-aside sensor 506 could be used but somehow moved from one side of the combine 500 to the other, either by hand before the crop is harvested or automatically with a positioning system. Alternately, the look-aside sensor 506 could be placed on just one side of the combine 500 permanently, requiring the operator to always move through the field in such that the permanently-mounted sensor 506 is always facing the subsequent pass in the field.

Because the look-aside sensor 506 is looking to the side of the combine 500 (that is, at the crop mass 610 to one side or other of the combine 500), the first pass through the field will not have any stored crop mass data to rely on.

It is important to note that one major difference in the processing for a look-aside version of the sensor 506 versus the look-head version is that the crop mass detected at any given time must be stored for later use, along with a location for which the stored data applies. That is, the data collected on the first pass (or the current pass) will need to contain some kind of location such that the data can be used at the appropriate point of travel on the subsequent pass. It is also possible that the crop mass reading from the look-aside sensor can be saved and reused by the machine at a future time, should harvesting be interrupted.

Another important note about the look-aside sensor is that, as it is not sensing an area of crop that is immediately going to enter the combine doing the sensing, then the crop mass information can be transmitted to other machines working in the same field. Jumping ahead in the figures to FIG. 6J, this figure illustrates the concept. In this example scenario, three separate combines (labeled 500A, 500B, and 500C to distinguish them in the figure, but identical otherwise in function to combine 500 on other drawings) are harvesting in a field together. This is a common scenario for contract harvesting companies that travel from field to field and harvest fields as a pay service for farmers. Although FIG. 6J shows the combines traveling in the field in the same direction, slightly staggered, other relationships in placement and direction of travel are possible without deviating from the intent of the invention.

As combine 500A travels through the field, harvesting plants 610, is uses its look-aside sensor 506 to sense the plants 610 in the next swath over from its current position. This information is then transmitted via a wireless communications link 688 to combine 500B, so that combine 500B can see the mass that it will be coming into. Combine 500B does the same for combine 500C.

It should be noted that the crop mass information may be transmitted to all harvesting machines on the field, and not necessarily to one specific machine. If one of the machines is taken out of service, then all machines have the same crop mass data, which also contains location data. Whichever combine machine gets to that "sensed area" first will use the crop mass data thus received to configure the combine accordingly, or to report to the operator for their information.

Figures 6D, 6E:
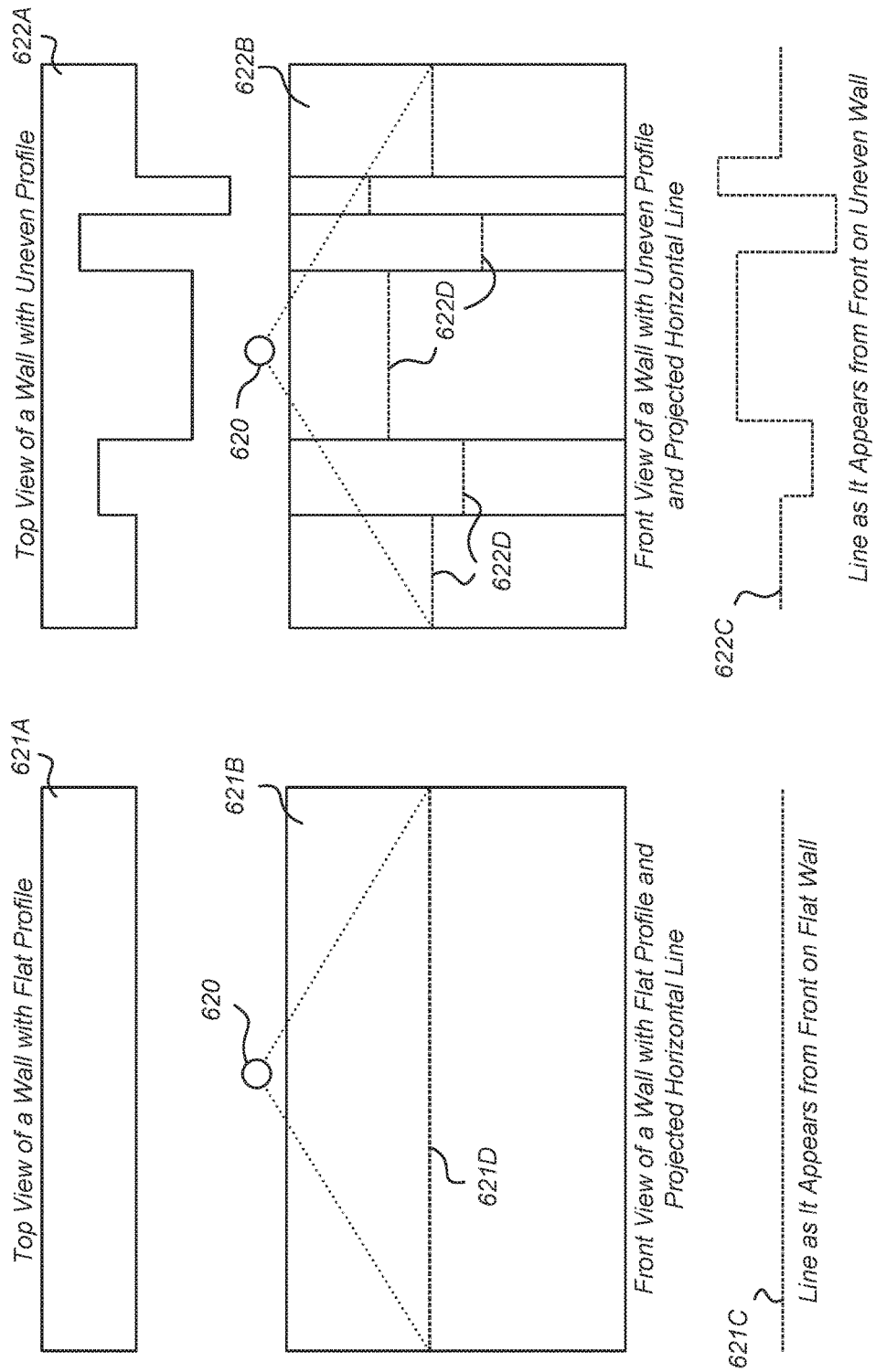

FIGS. 6D through 6J illustrate an alternate embodiment of the LIDAR portion of the crop mass sensor 506. FIG. 6D illustrates how a horizontal line of light 621D emitted by a laser device 620 appears to be straight when displayed on a flat wall surface. The wall shape assumed in FIG. 6D is shown in a top view 621A (showing the wall's profile), and a front view 621B (showing how the horizontal line of light will be seen when viewed from the front on a flat wall. The perceived line 621C when seen from the front view is a straight horizontal line profile.

FIG. 6E illustrates how a horizontal line of light 622D emitted by a laser device 620 appears to be "broken" or displayed in "stair steps" when displayed on an uneven wall surface. The wall shape assumed in FIG. 6E is shown in a top view 622A (showing the wall's profile, which has varying thickness or depth depending on which portion of the wall you are looking at), and a front view 622B (showing how the horizontal line of light will be seen when viewed from the front on an uneven wall. The perceived line 622C when seen from the front view is a line consisting of a series of steps, where portions of the displayed line 622D hit a section of wall that is closer to the laser 620 versus how the steps are displayed when the line 622D is displayed on sections of wall that are farther away.

Figure 6G:
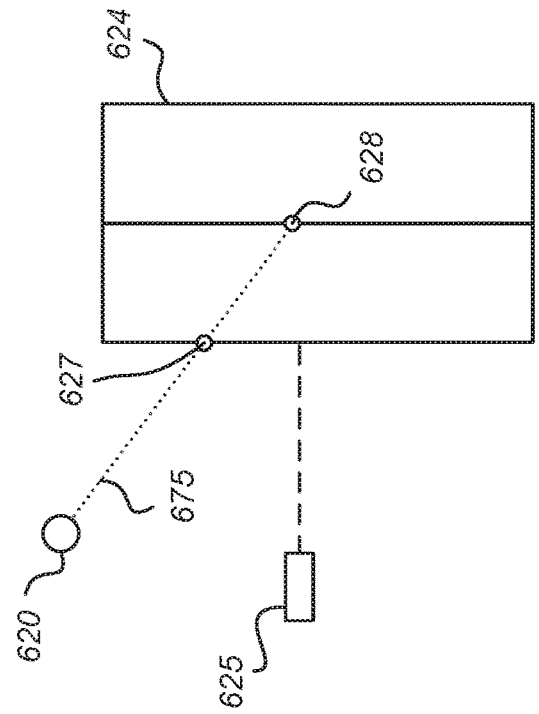
Figure 6F:
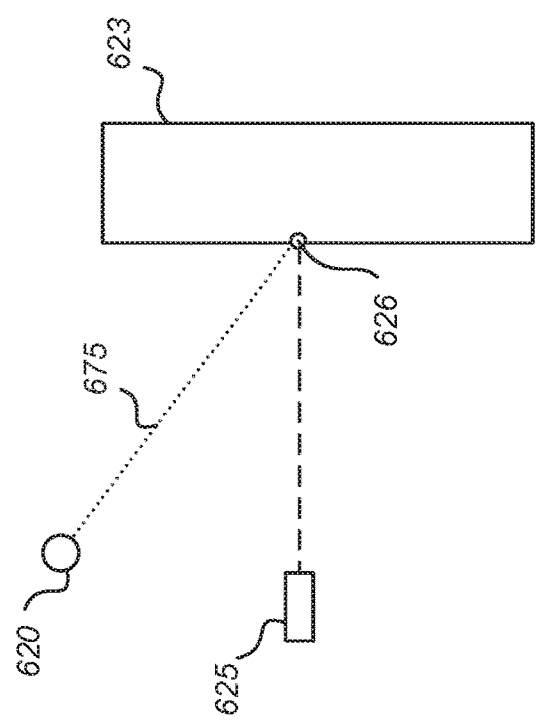

This concept may be better understood by looking at FIGS. 6F and 6G. FIG. 6F shows the side view 623 of the flat wall section of FIG. 6D. From this view, it becomes apparent that the laser 620 should shine on the wall from an angle that is not perpendicular to the wall, and that the result should be viewed from an angle that is more or less perpendicular to the wall. An imaging device 625, such as a camera, is placed at an angle that is substantially perpendicular to the wall. A line will appear on wall 623 at a point 626 where the light beam 675 strikes the wall.

FIG. 6G shows the side view 624 of the uneven wall section of FIG. 6E. When an uneven wall 624 is used, the emitted light beam 675 will strike the wall section 624 sooner for sections of wall 627 that are closer to the laser 620, and later for sections of wall 628 that are farther back from the laser 620. When an imaging device 625, such as a camera, placed at an angle that is substantially perpendicular to the wall, views the line, segments of the line will appear higher when displayed on sections of wall that are closer 627, and other segments that are farther back 628 will display the line in a position that is relatively lower.

Figure 6H:
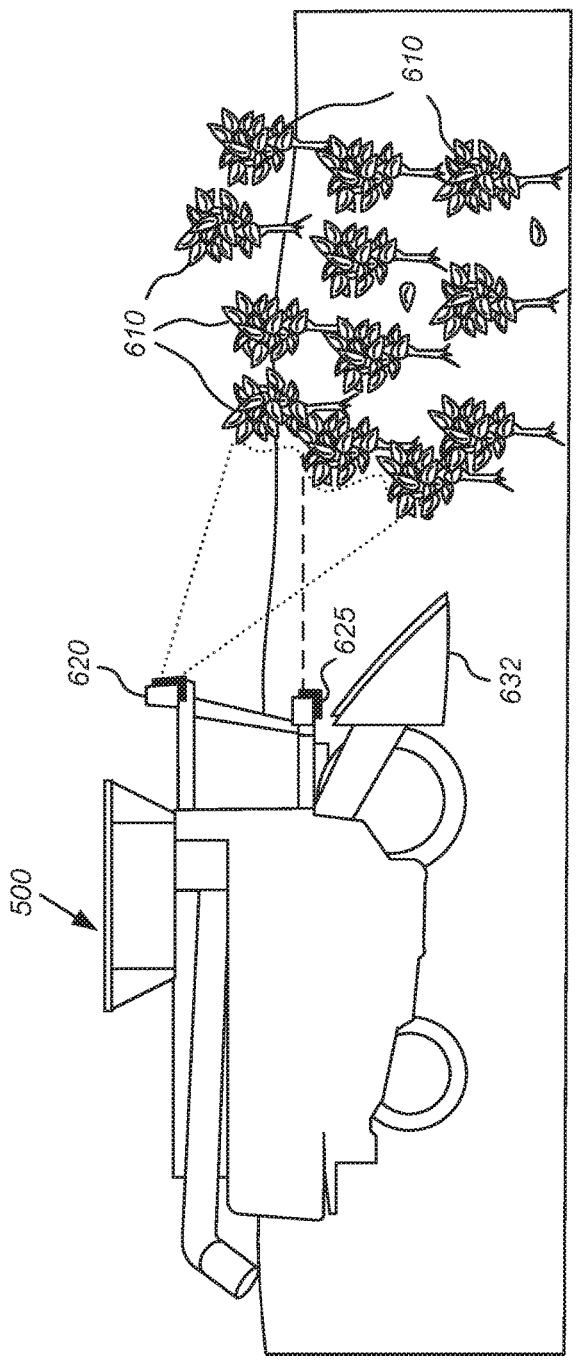

FIG. 6H shows how the "structured light" concept for detecting the uneven surface of a wall (as illustrated in FIGS. 6D through 6G) can be extended to detecting crop mass in an agricultural situation. If the laser 620 is mounted higher up on the combine 500 and projects a horizontal line on the front "wall" of the crop material 610 that it is approaching, the perceived line when seen from an imaging device 625 that is mounted in a position such that it perceives the line from an angle that is approximately perpendicular to the direction of travel of the combine 500 will appear to be distorted, with some sections of the perceived line being higher than others.

Figure 6I:
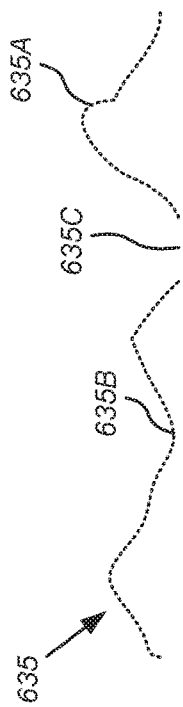

Looking at FIG. 6I, we see one example of a perceived line 635 that might appear in an image from an imaging device 625 perceiving the line as described above. The line will appear to be higher in spots where the horizontal line is displayed on crop material 610 that is closer to laser 620 and lower in spots where the line is displayed on crop material 610 that is farther away from the laser 620.

For example, location 635B appears to be the lowest point of perceived line 635, indicating that this spot corresponds to the point on the crop material 610 that is farthest from the laser 620. Similarly, location 635A appears to be the highest point of perceived line 635, indicating that this spot corresponds to the point on the crop material 610 that is closest to the laser 620. A break or gap 635C in the perceived line 635 likely indicates an area where there was no crop material 610 at all, or where the crop material 610 was too far from the combine to be detected, since there would be no surface onto which the perceived line 635 could be displayed.

The shape of perceived line 635 can thus be used to gather data on the shape of the front wall of the mass of crop material 610 as a combine 500 moves through a field, and this shape information can be used to create a three-dimensional model of the crop mass before it is pulled into the combine 500 itself.

IX. Mobile Device User Interface

FIGS. 7A-7C show aspects of one embodiment of an application user interface for the present invention as displayed on a mobile computing device. In at least one embodiment, the combine automation system of the present invention has the ability to communicate wirelessly with external devices, which may include mobile devices such as smart phones, tablet computers (such as the iPad by Apple), laptops, other vehicles, and any other appropriate mobile device. In at least one embodiment, the combine automation system of the present invention uses a mobile device as a display and user interface.

Turning to FIG. 7A, we see one embodiment of an application user interface for the present invention as displayed on a mobile computing device 700. The mobile device 700 has a display screen 702 which may be used as a system display, showing the status of the system and the results gathered by or calculated from the system sensors previously described in this specification. In this example page in FIG. 7A, a graphical representation 706 of the combine is displayed, and important values such as sensor readings 704 are displayed superimposed or proximal to the graphical representation 706. Since display 702 is a computer display, the actual readings and types of graphics displayed are virtually unlimited, but as shown in FIG. 7A typical sensor values 704 may include the percentage of damaged (cracked) grain, the percentage of MOG, the moisture content of the grain, the grain yield, the combine speed and engine RPMs, settings of the cleaning shoe and other combine subsystems, and productivity information (such as acres per hour). The display 702 can be used to send system messages to the operator. These messages may include directives such as a recommendation to increase or decrease speed depending on the sensed condition of the harvested crop.

FIG. 7B shows another embodiment of an application user interface page for the present invention as displayed on a mobile computing device 700. In this example page, a "pop up" window 708 is displayed on the display screen 702. This pop up window 708 may include detailed information on a combine subsystem or may allow access to a user control. In the example shown in FIG. 7B, the pop up window 708 shows a system control 714 which allows the operator in select the best operating mode for the combine. The circle control shown on system control 714 can be moved over the triangular shape by the operator to command that the system focus more on certain harvesting parameters than others. Once the proper set point is selected, the operator can commit that by pressing the "set" key 710. Once the desired attributes are selected, the algorithms controlling automatic combine adjustment will use this information to determine how to set the combine's system parameters.

FIG. 7C shows yet another embodiment of an application user interface page for the present invention as displayed on a mobile computing device 700. In this example, a subwindow 712 showing the images of cracked grain is displayed in the main window 702.

All of the example pages shown in FIGS. 7A through 7C are examples only and not meant to be limiting in any way.

X. Control System and Algorithms

Figure 8:
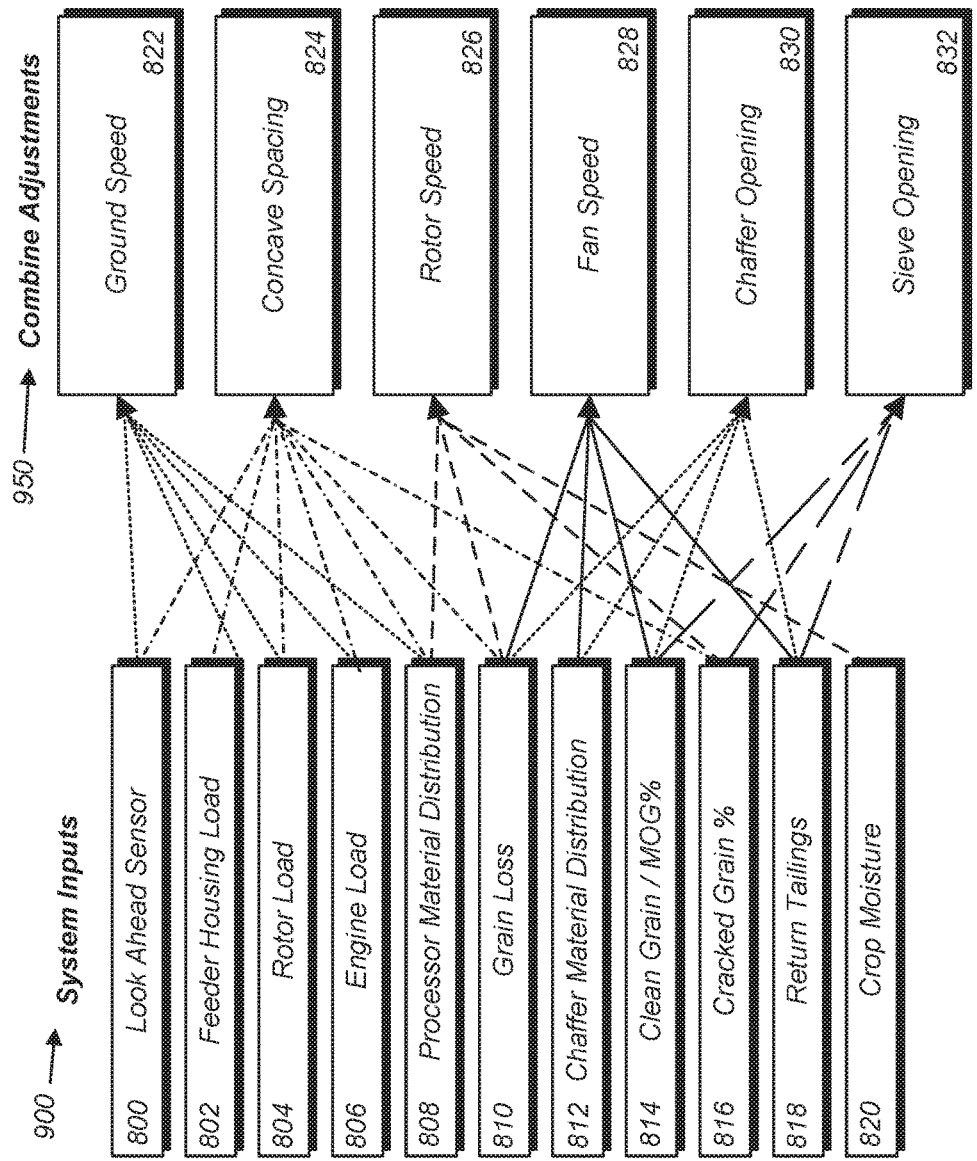
FIG. 8 shows a series of combine adjustments that may be made by the present invention, as well as the system inputs that are used to determine what adjustments are to be made.

FIG. 8 shows a series of combine adjustments that may be made by the present invention, as well as the system inputs that are used to determine what adjustments are to be made. Focusing first on the right most column of the figure, we see a list of combine adjustments 950 that can be made and which affect the quality and/or quantity of the grain successfully harvested.

The combine adjustments 950 are the system parameters that can be changed to try to find the optimal operating efficiency of a combine, and they comprise the ground speed 822, concave setting 824, rotor speed 826, fan speed 828, chaffer opening 830, and sieve opening 832.

Each of these adjustments 950 may have an effect on the operational efficiency of the combine:

If the ground speed 822 is too fast, then it is possible that the plant material being pulled into the combine will overload the machine and cause a jam; it the ground speed 822 is too slow then the machine may be underused.

If the concave spacing 824 is too close, movement against the rotor may cause damage to the grain; if the concave spacing 824 is too far, then the grain may not be fully threshed.

If the rotor speed 826 is too fast, the plant material may bind up and overload the rotor; if the rotor speed 826 is too slow, proper threshing may not occur.

If the fan speed 828 is too fast, then the air stream it generates may blow clean grain out the back along with the lighter chaff and MOG; if the fan speed 828 is too slow, then the air may not be strong enough to sufficiently lift MOG out of the clean grain.

If the chaffer opening 830 is too open, then bits of MOG may fall through along with the clean grain; if the chaffer opening 830 is too closed, the clean grain may not pass through.

If the sieve opening 832 is too open, then bits of MOG may fall through along with the clean grain; if the sieve opening 832 is too closed, the clean grain may not pass through.

The if-then statements provided in the bullets immediately preceding this paragraph are provided as examples of behavior that may be seen in some embodiments of the present invention, and they are not meant to be limiting. Other relationships between system inputs 900 and combine adjustments 950 may exist in other embodiments of the present invention. There may also be other system inputs 900, or some of those system inputs 900 presented herein may be removed or altered, in other embodiments of the present invention. The same applies to the combine adjustments 950. The combine system represented in these examples is one possible embodiment, and alternate embodiments of this architecture may exist without deviating from the present invention.

The combine control system must be able to determine when each of these combine adjustments 950 is improperly set without human intervention in order for the automation of the combine to be realized. In order to do this, the combine control system will look at various combinations of the system inputs 900 to determine which combine adjustments 950 are improperly set. Arrows are drawn from each system input 900 out to each of the combine adjustments 950 that they correspond to.

For example, the following system inputs 900 are used, individually or in combination, to determine of the ground speed 822 is too low or too high:

Look Ahead Sensor 800
Feeder Housing Load 802
Rotor Load 804
Engine Load 806
Processor Material Distribution 808
Grain Loss 810
Chaffer Material Distribution 812
Clean Grain/MOG % 814
Cracked Grain %
Return Tailings 818
Crop Moisture 820

The values taken from these 5 system inputs 900 help the combine automation system determine if the ground speed 822 needs to be adjusted. If the look ahead sensor 800 shows that a large mass of crop is about to enter the machine, than the combine automation system may recommend that the ground speed 822 be lowered so that the combine can handle the increased load. All of the system inputs 900 that are used in calculating the appropriate ground speed setting 822 are load based. That is, they all provide information on the load the machine is either currently managing, or is about to. If there is too much mass or load on the system, the ground speed 822 needs to be lowered.

The other combine adjustments 950 are determined in a similar fashion.

Figure 9:
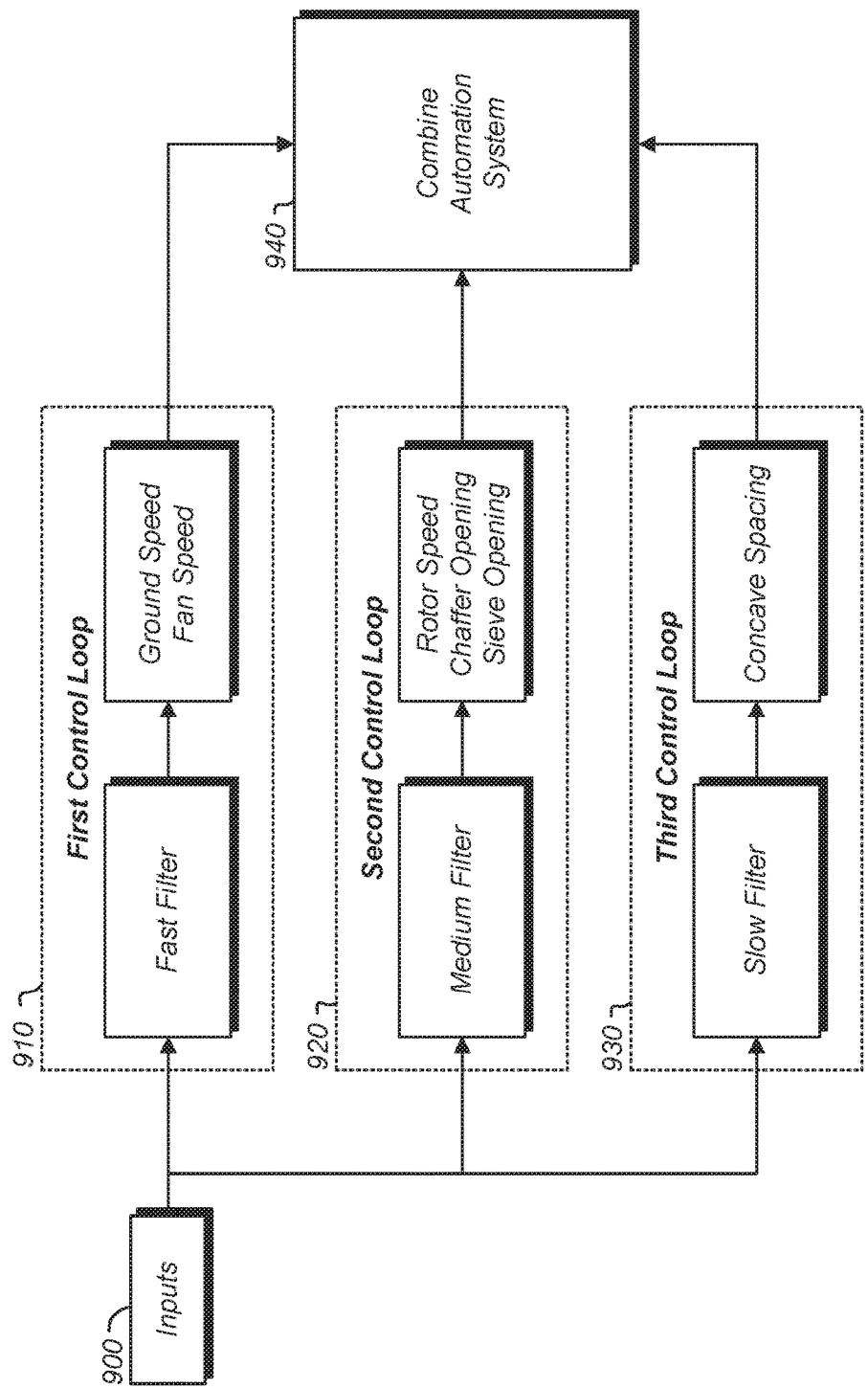
FIG. 9 shows one embodiment of a control system architecture for the present invention.

FIG. 9 shows one embodiment of a control system architecture for the present invention. The control system consists of three tiers. At the top tier 910, the system inputs 900 are filtered with a fast low-pass filter. The control outputs are evaluated once per second and control the ground speed 822 and fan speed 828 combine adjustments 950. These outputs are sent to the combine automation system 940, which uses the information from the outputs to change the appropriate combine adjustments 950.

The next tier 920 will use a slower low-pass filter on the system inputs 900. The control outputs are evaluated once per minute, and control the rotor speed 826, chaffer opening 830, and sieve opening 832.

The last tier 930 will use a very slow low-pass filter on the system inputs 900. The control outputs are evaluated once every 15 minutes and control the concave spacing 824.

FIGS. 10A through 10N are a series of flowcharts which capture logic that may be used by the present invention to determine which combine adjustments to make. It is important to note that FIGS. 10A through 10N are provided as examples of logic that may be used in one or more embodiments of the present invention, but they are not meant to be limiting in any way. Other logic arrangements may exist and may be used in other embodiments without deviating from the inventive concept of the present invention.

FIG. 10A shows four conditions which can be used individually or in combination to determine if the ground speed is too fast. These conditions are the material distribution being toward the back of the combine, high power and high fuel usage, high rotor torque, and high feeder load.

FIG. 10B shows four conditions which can be used individually or in combination to determine if the ground speed is too slow. These conditions are the material distribution being toward the front of the combine, low power and low fuel usage, low rotor torque, and low feeder load.

Figure 10D:
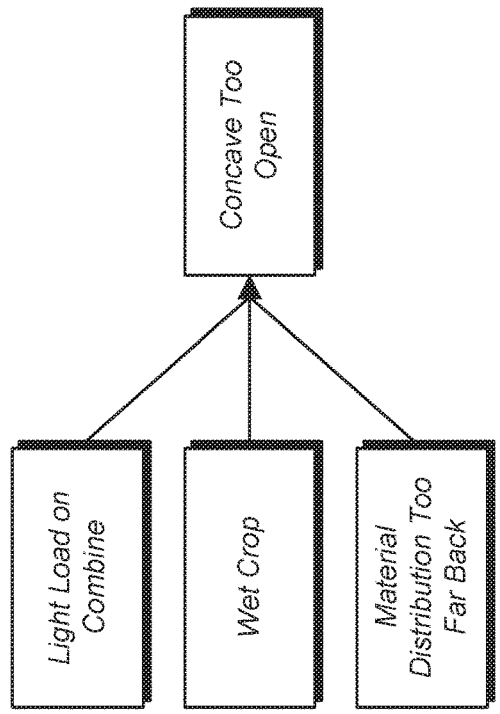
FIGS. 10A through 10N are a series of flowcharts which capture logic that may be used by the present invention to determine which combine adjustments to make.
Figure 10C:
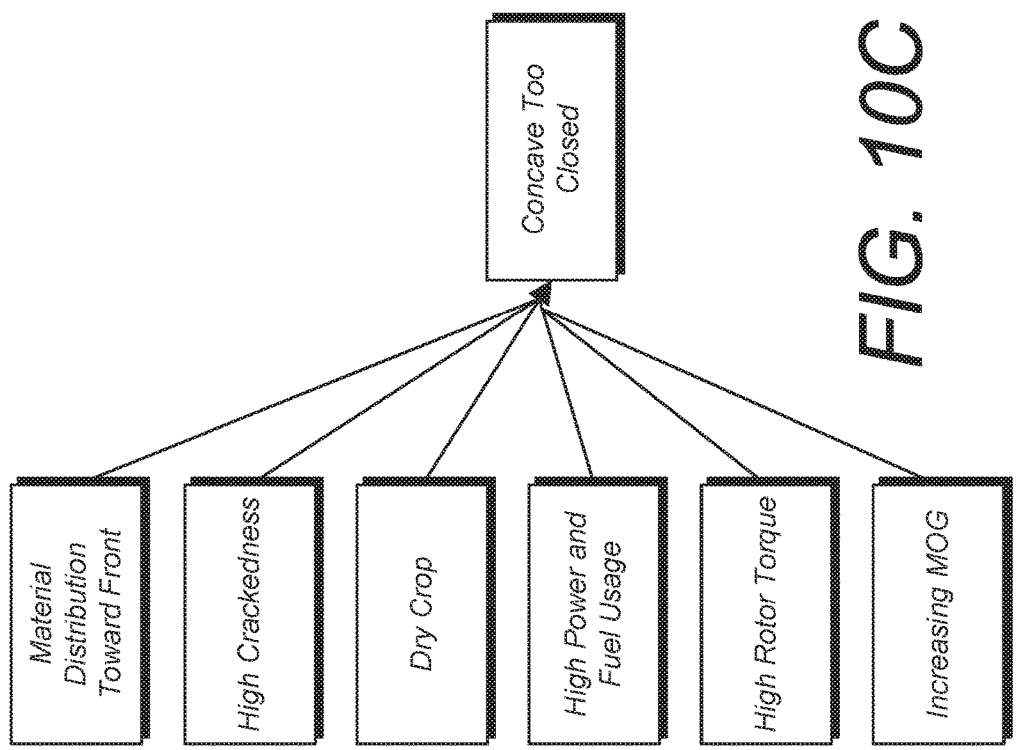

FIG. 10C shows six conditions which can be used individually or in combination to determine if the concave is too closed. These conditions are the material distribution being toward the front of the combine, a high amount of cracked or damaged grain, a low moisture content in the crop (dry crop), high power and high fuel usage, high rotor torque, and an increasing level of MOG in the grain.

FIG. 10D shows three conditions which can be used individually or in combination to determine if the concave is too open. These conditions are a light combine load, a high moisture content in the crop (wet crop), and material distribution being shifted too far back.

FIG. 10E shows one condition which can be used to determine if the rotor speed should be minimized, and this condition is a low moisture content in the crop.

FIG. 10F shows one condition which can be used to determine if the rotor speed should be maximized, and this condition is a high moisture content in the crop.

FIG. 10G shows one condition which can be used to determine if the rotor speed should be decreased, and this condition is a high percentage of cracked or damaged grain.

FIG. 10H shows two conditions which can be used to determine if the rotor speed should be increased, and these conditions are material distribution shifted to the back and a high processor loss.

FIG. 10I shows two conditions which can be used to determine if the fan speed should be increased, and these conditions are a high percentage of MOG seen at the chaffer and a high amount of returns.

FIG. 10J shows two conditions which can be used to determine if the fan speed should be decreased, and these conditions are a high loss seen at the chaffer and chaffer distribution is shifted toward the back.

FIG. 10K shows three conditions which can be used to determine if the chaffer opening should be closed down, and these conditions are a high percentage of MOG seen at the hopper, a high amount of returns, and a high percentage of MOG seen at the chaffer.

FIG. 10L shows one condition which can be used to determine if the chaffer opening should be opened up, and this condition is a high sloughing loss.

FIG. 10M shows one condition which can be used to determine if the sieve opening should be closed, and this condition is a high amount of MOG as seen at the hopper.

FIG. 10N shows one condition which can be used to determine if the sieve opening should be opened up, and this condition is a high amount of returns.

XI. Membership Functions

In one embodiment, the main combine automation control system is a fuzzy inference system based on the cause/effect diagrams shown in FIGS. 10A through 10N. The system inputs 900 are mapped into fuzzy membership functions as shown in Table 1 below. Then the outputs are mapped to fuzzy membership functions as shown in Table 2. Finally, several combine automation rules are created to determine the behavior of the combine automation system, as shown in Table 3.

TABLE 1

Mapping of System Inputs

| Variable | Input | MF1 | MF2 | MF3 |
|---|---|---|---|---|
| 1 | LookAhead | low | ideal | high |
| 2 | FeederTorque | low | ideal | high |
| 3 | RotorTorque | low | ideal | high |
| 4 | EngineLoad | low | ideal | high |
| 5 | ProcessorMADS | ideal | back | |
| 6 | ProcessorLoss | low | ideal | high |
| 7 | ChafferLoss | low | ideal | high |
| 8 | BlowingLoss | low | ideal | high |

TABLE 1-continued

Mapping of System Inputs

| Variable | Input | MF1 | MF2 | MF3 |
|---|---|---|---|---|
| 9 | ChafferMADS | ideal | back | |
| 10 | ChafferMOG | ideal | high | |
| 11 | HopperMOG | low | ideal | high |
| 12 | CrackedGrain | low | ideal | high |
| 13 | Tailings | low | ideal | high |
| 14 | Moisture | dry | ideal | wet |
| 15 | Optimization | loss | groundSpeed | cleanliness |

TABLE 2

Mapping of System Outputs (the Combine Adjustments)

| Variable | Output | MF1 | MF2 | MF3 |
|---|---|---|---|---|
| 1 | Ground Speed | low | ideal | high |
| 2 | Rotor Speed | tooFast | ideal | tooSlow |
| 3 | Concave | tooClosed | ideal | tooOpened |
| 4 | Fan Speed | tooFast | ideal | tooSlow |
| 5 | Chaffer Opening | tooClosed | ideal | tooOpened |
| 6 | Sieve Opening | tooClosed | ideal | tooOpened |

TABLE 3

Combine Automation System Rules

1. If (LookAhead is high) or (FeederTorque is high) or (RotorTorque is high) or (ProcessorMADS is back) or (ProcessorLoss is high) then (GroundSpeed is high) (0.5)
2. If (LookAhead is low) or (FeederTorque is low) or (RotorTorque is low) or (ProcessorLoss is low) then (GroundSpeed is slow) (0.5)
3. If (EngineLoad is high) then (GroundSpeed is high) (1)
4. If (EngineLoad is low) then (GroundSpeed is slow) (1)
5. If (CrackedGrain is high) then (RotorSpeed is tooFast) (1)
6. If (ProcessorMADS is back) or (ProcessorLoss is high) then (RotorSpeed is tooSlow) (1)
7. If (Moisture is dry) then (RotorSpeed is tooFast) (0.5)
8. If (Moisture is wet) then (RotorSpeed is tooSlow) (0.5)
9. If (RotorTorque is high) or (EngineLoad is high) or (ProcessorLoss is high) or (ChafferLoss is high) or (ChafferMOG is ideal) or (CrackedGrain is high) then (Concave is tooClosed) (1)
10. If (RotorTorque is low) or (EngineLoad is low) then (Concave is tooOpened) (1)
11. If (BlowingLoss is low) or (ChafferMADS is back) or (ChafferMOG is ideal) or (Tailings is high) then (FanSpeed is tooSlow) (1)
12. If (BlowingLoss is high) then (FanSpeed is tooFast) (1)
13. If (ChafferLoss is high) then (ChafferSpacing is tooClosed) (1)
14. If (ChafferLoss is low) or (ChafferMOG is ideal) or (HopperMOG is ideal) or (Tailings is high) then (ChafferSpacing is tooOpened) (1)
15. If (HopperMOG is high) then (SieveSpacing is tooOpened) (1)
16. If (Tailings is high) then (SieveSpacing is tooClosed) (1)

Having described the preferred embodiments, it will become apparent that various modifications can be made without departing from the scope of the invention as defined in the accompanying claims.

The examples and processes defined herein are meant to be illustrative and describe only particular embodiments of the invention.

Having thus described the invention, what is claimed as new and desired to be secured by Letters Patent is:

1. A harvesting machine comprising:
   a grain elevator having a conveyor belt with upper and lower ends positioned within said harvesting machine and configured for lifting a harvested crop within said harvesting machine;
   an on-board processor having a non-volatile memory;

said processor configured for controlling crop harvesting and weighing operation parameters;

first and second weight sensors operably connected at first and second sides of said conveyor belt upper end at approximately equal elevations;

each said weight sensor configured for providing an output corresponding to a portion of the conveyor belt weight on a respective conveyor belt upper end first or second side;

each said weight sensor output comprising an input to said processor;

a moisture sensor configured for determining the moisture content of said harvested crop and for providing an output corresponding to said moisture content of said harvested crop;

said moisture sensor output comprising an input to said processor;

said processor configured for processing data received from said weight and moisture sensors;

said processor configured for initializing with an empty conveyor belt weight;

each said weight sensor configured for providing an output to said processor comprising a loaded conveyor belt weight while said conveyor belt is lifting said harvested crop;

said processor configured for subtracting said empty conveyor belt weight from said loaded conveyor belt weight to determine a weight of harvested crop on each side of said conveyor belt;

said processor configured for automatically adjusting said crop harvesting parameters of said harvesting machine based on said weight and said moisture content of said harvested crop and to compensate for any asymmetrical weight conditions on said conveyor belt; and wherein said crop harvesting parameters are selected from the group consisting of: harvesting machine speed; direction; crop quality; engine RPM; sieve spacing; harvester machine fan-rotor speed; and combinations thereof.

2. The harvesting machine according to claim 1, wherein:
said weight sensors comprise potentiometers configured for providing output corresponding to deflection of said conveyor belt upper end sides.

3. The harvesting machine according to claim 1, wherein:
said grain elevator comprises a clean grain elevator; and
said harvesting machine further comprises a clean grain tank for receiving clean grain from said clean grain elevator.

4. The harvesting machine according to claim 1, further comprising:
look-ahead and look-aside sensors configured for estimating crop mass ahead of and alongside said harvesting machine respectively.

5. A system for estimating the weight of a crop harvested in a harvesting machine including a grain elevator having a conveyor belt with upper and lower ends positioned within the harvesting machine and an on-board processor with a non-volatile memory, said processor controlling crop harvesting and weighing operations, which system comprises:

first and second weight sensors operably connected at first and second sides of said conveyor belt upper end at approximately equal elevations;

each said weight sensor configured for providing an output corresponding to a portion of the conveyor belt weight on a respective conveyor belt upper end first or second side;

wherein said weight sensors comprise potentiometers configured for providing output corresponding to deflection of said conveyor belt upper end sides;

each said weight sensor output comprising an input to said processor;

said processor configured for processing data received from said weight sensors;

said processor configured for initializing with an empty conveyor belt weight;

said elevator configured for lifting said harvested crop within said harvesting machine;

each said weight sensor configured for providing an output to said processor comprising a loaded conveyor belt weight while said conveyor belt is lifting said harvested crop;

said processor configured for subtracting said empty conveyor belt weight from said loaded conveyor belt weight to determine a weight of harvested crop on each side of said conveyor belt;

said processor configured for providing output corresponding to said harvested crop weight;

said processor configured for adjusting crop harvesting parameters to compensate for asymmetrical weight conditions on said conveyor belt; and wherein said crop harvesting parameters are selected from the group consisting of: harvesting machine speed; direction; crop quality; engine RPM; sieve spacing; harvester machine fan-rotor speed; and combinations thereof.

6. The system for estimating the weight of a crop harvested in a harvesting machine according to claim 5, wherein:
said grain elevator comprises a clean grain elevator; and
said harvesting machine further comprises a clean grain tank for receiving clean grain from said clean grain elevator.

7. The system for estimating the weight of a crop harvested in a harvesting machine according to claim 5, further comprising:
a moisture sensor configured for determining the moisture content of said harvested crop and providing a corresponding input representing said moisture content to said processor.

* * * * *